(12) United States Patent
Turner, Jr. et al.

(10) Patent No.: US 6,929,937 B2
(45) Date of Patent: Aug. 16, 2005

(54) HUMAN TRANSFERASE PROTEINS AND POLYNUCLEOTIDES ENCODING THE SAME

(75) Inventors: C. Alexander Turner, Jr., The Woodlands, TX (US); Glenn Friedrich, Houston, TX (US); Alejandro Abuin, The Woodlands, TX (US); Brian Zambrowicz, The Woodlands, TX (US); Arthur T. Sands, The Woodlands, TX (US); D. Wade Walke, Spring, TX (US); Nathaniel L. Wilganowski, Houston, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 10/364,774

(22) Filed: Feb. 11, 2003

(65) Prior Publication Data

US 2003/0144497 A1 Jul. 31, 2003

Related U.S. Application Data

(62) Division of application No. 09/795,926, filed on Feb. 28, 2001, now Pat. No. 6,555,669.
(60) Provisional application No. 60/185,920, filed on Feb. 29, 2000, provisional application No. 60/186,558, filed on Mar. 2, 2000, and provisional application No. 60/191,849, filed on Mar. 24, 2000.

(51) Int. Cl.[7] .............................. C12N 9/10; C07H 21/04
(52) U.S. Cl. ...................................... 435/193; 536/23.2
(58) Field of Search ........................ 435/193; 536/23.2; 530/327, 350

(56) References Cited

U.S. PATENT DOCUMENTS

| | | | |
|---|---|---|---|
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,689,405 A | 8/1987 | Frank et al. |
| 4,713,326 A | 12/1987 | Dattagupta et al. |
| 4,946,778 A | 8/1990 | Ladner et al. |
| 5,252,743 A | 10/1993 | Barrett et al. |
| 5,424,186 A | 6/1995 | Fodor et al. |
| 5,445,934 A | 8/1995 | Fodor et al. |
| 5,459,127 A | 10/1995 | Felgner et al. |
| 5,556,752 A | 9/1996 | Lockhart et al. |
| 5,700,637 A | 12/1997 | Southern |
| 5,744,305 A | 4/1998 | Fodor et al. |
| 5,837,458 A | 11/1998 | Minshull et al. |
| 5,877,397 A | 3/1999 | Lonberg et al. |
| 5,948,767 A | 9/1999 | Scheule et al. |
| 6,075,181 A | 6/2000 | Kucherlapati et al. |
| 6,110,490 A | 8/2000 | Thierry |

OTHER PUBLICATIONS

White et al. J. Biol. Chem. (1995), vol. 270, pp. 24156–24165.*
Bennett (Nov. 27, 2002) GenBank accession AJ505950.*
Cheng et al. FEBS Letters (2002), vol. 531, pp. 115–121.*
Ansorge et al. (Jul. 8, 1999) GenBank accession AL096739.*
Bird et al, 1988, "Single–Chain Antigen–Binding Proteins", Science 242:423–426.
Bitter et al, 1987, "Expression and Secretion Vectors for Yeast", Methods in Enzymology 153:516–544.
Colbere–Garapin et al, 1981, "A New Dominant Hybrid Selective Marker for Higher Eukaryotic Cells", J. Mol. Biol. 150:1–14.
Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.
Gordon, 1989, "International Review of Cytology", 115:171–229.
Greenspan et al, 1993, "Idiotypes: structure and immunogenicity", FASEB Journal 7:437–444.
Huse et al, 1989, "Generation of a Large Combinatorial Library of the Immunoglobulin Repertoire in Phage Lambda", Science 246:1275–1281.
Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.
Inoue et al, 1987, "Sequence–dependent hydrolysis of RNA using modified oligonucleotide splints and R Nase H", FEBS Letters 215(2):327–330.
Inoue et al, 1987, "Synthesis and hybridization studies on two complementary nona(2'–O–methyl)ribonucleotides", Nucleic Acids Research 15(15):6131–6149.
Inouye & Inouye, 1985, "Up–promoter mutations in the lpp gene of *Escherichia coli*", Nucleic Acids Research 13(9):3101–3110.
Janknecht et al, 1991, "Rapid and efficient purification of native histidine–tagged protein expressed by recombinant vaccinia virus", PNAS 88:8972–8976.
Kohler & Milstein, 1975, "Continuous cultures of fused cells secreting antibody of predefined specificity", Nature 256:495–497.
Logan et al, 1984, "Adenovirus tripartite leader sequence enhances translation of mRNAs late after infection", Proc. Natl. Acad. Sci. USA 81:3655–3659.
Lowy et al, 1980, "Isolation of Transforming DNA: Cloning the Hamster aprt Gene", Cell 22:817–823.

(Continued)

*Primary Examiner*—Elizabeth Slobodyansky

(57) ABSTRACT

Novel human polynucleotide and polypeptide sequences are disclosed that can be used in therapeutic, diagnostic, and pharmacogenomic applications.

1 Claim, No Drawings

OTHER PUBLICATIONS

McKinlay et al, 1989, "Rational Design of Antiviral Agents", Annu. Rev. Pharmacol. Toxicol. 29:111–122.

Miyajima et al, 1986, "Expression of murine and human granulocyte–macrophage colony–stimulating factors in *S. cerevisiae*: mutagenesis of the potential glycosylation sites", The EMBO Journal 5(6):1193–1197.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Platt, K.A. et al, 1994, "Independent Regulation of Adipose Tissue–specificity and Obesity Response of the Adipsin Promoter in Transgenic Mice", The Journal of Biological Chemistry 269(46):28558–28562.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the *Autographa californica* Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

Sakakibara Yoichi et al: "Molecular cloning, expression, and characterization of novel human SULT1C sulfotransferases that catalyze the sulfonation of N–hydroxy–2–acetylaminofluorene.", Journal of Biological Chemistry, vol. 273, No. 51, Dec. 18, 1998, pp. 33929–33935, XP002190183.

Copy of International Search Report (PCT/US01/06460).

* cited by examiner

SEQUENCE LISTING

<160> NUMBER OF SEQ ID NOS: 47

<210> SEQ ID NO 1
<211> LENGTH: 912
<212> TYPE: DNA
<213> ORGANISM: homo sapiens

<400> SEQUENCE: 1

```
atgctgata aatccaaatt tattgaatac attgacgaag ctttagaaaa atcaaaagaa      60
actgcactct ctcatttatt tttcacctat caggggattc cttacccat caccatgtgc      120 acctcagaaa ctttccaagc gctggacacc ttcgaagcca gacatgatga catcgtgcta      180
gcatcttatc caaagtgcgg ttcaaactgg attctccaca ttgtcagtga attaatatat     240
gctgtttcta aaaaaagta taaatatcca gaattcccag ttcttgaatg tggggattca      300
gaaaaatatc agagaatgaa aggctttcca tcaccaagga ttttggcaac tcacctccac    360
tatgacaaat tacctgggtc tatcttcgag aataagcca agatattggt gatatttcga     420
aaccctaaag atacagcagt atctttttg catttccaca acgatgtccc cgatattcca     480
agctatggct cttgggatga attcttcaga cagttcatga aggacaagt ttcttgggga     540 aggtattttg attttgcaat caattggaac aaacatcttg atggcgacaa tgttaagttc     600
atattatatg aagacctgaa agagaatctg gctgctggaa taaaacagat tgctgagttc     660
ttgggattct ttctaactgg ggagcaaatt caaactatct cagtccagag caccttccaa    720
gccatgcgtg cgaagtctca ggacacacac ggtgctgtcg gcccattcct tttccgcaaa     780
ggtgaagttg tgattggaaa aaatttgttc agtgaaattc agaaccagga aatggatgaa     840
aaattcaaag agtgcttagc aggcacctcc ctcggagcaa agttgaagta tgaatcatat    900
```

-continued tgccagggtt ga                                                    912

<210> SEQ ID NO 2
<211> LENGTH: 303
<212> TYPE: PRT
<213> ORGANISM: homo sapiens

<400> SEQUENCE: 2

Met Ala Asp Lys Ser Lys Phe Ile Glu Tyr Ile Asp Glu Ala Leu Glu
 1               5                  10                  15

Lys Ser Lys Glu Thr Ala Leu Ser His Leu Phe Phe Thr Tyr Gln Gly
            20                  25                  30

Ile Pro Tyr Pro Ile Thr Met Cys Thr Ser Glu Thr Phe Gln Ala Leu
        35                  40                  45

Asp Thr Phe Glu Ala Arg His Asp Asp Ile Val Leu Ala Ser Tyr Pro
    50                  55                  60

Lys Cys Gly Ser Asn Trp Ile Leu His Ile Val Ser Glu Leu Ile Tyr
65                  70                  75                  80

Ala Val Ser Lys Lys Tyr Lys Tyr Pro Glu Phe Pro Val Leu Glu
                85                  90                  95

Cys Gly Asp Ser Glu Lys Tyr Gln Arg Met Lys Gly Phe Pro Ser Pro
            100                 105                 110

Arg Ile Leu Ala Thr His Leu His Tyr Asp Lys Leu Pro Gly Ser Ile
        115                 120                 125

Phe Glu Asn Lys Ala Lys Ile Leu Val Ile Phe Arg Asn Pro Lys Asp
    130                 135                 140

Thr Ala Val Ser Phe Leu His Phe His Asn Asp Val Pro Asp Ile Pro
145                 150                 155                 160

Ser Tyr Gly Ser Trp Asp Glu Phe Phe Arg Gln Phe Met Lys Gly Gln
                165                 170                 175

Val Ser Trp Gly Arg Tyr Phe Asp Phe Ala Ile Asn Trp Asn Lys His
            180                 185                 190

Leu Asp Gly Asp Asn Val Lys Phe Ile Leu Tyr Glu Asp Leu Lys Glu
        195                 200                 205

Asn Leu Ala Ala Gly Ile Lys Gln Ile Ala Glu Phe Leu Gly Phe Phe
    210                 215                 220

Leu Thr Gly Glu Gln Ile Gln Thr Ile Ser Val Gln Ser Thr Phe Gln
225                 230                 235                 240

Ala Met Arg Ala Lys Ser Gln Asp Thr His Gly Ala Val Gly Pro Phe
                245                 250                 255

Leu Phe Arg Lys Gly Glu Val Gly Asp Trp Lys Asn Leu Phe Ser Glu
            260                 265                 270

Ile Gln Asn Gln Glu Met Asp Glu Lys Phe Lys Glu Cys Leu Ala Gly
        275                 280                 285

Thr Ser Leu Gly Ala Lys Leu Lys Tyr Glu Ser Tyr Cys Gln Gly
    290                 295                 300

<210> SEQ ID NO 3
<211> LENGTH: 333
<212> TYPE: DNA
<213> ORGANISM: homo sapiens

<400> SEQUENCE: 3
atgtgcacct cagaaacttt ccaagcgctg gacaccttcg aagccagaca tgatgacatc    60
gtgctagcat cttatccaaa gtgcggttca aactggattc tccacattgt cagtgaatta   120

```
atatatgctg tttctaaaaa aaagtataaa tatccagaat tcccagttct tgaatgtggg    180
gattcagaaa aatatcagag aatgaaaggc tttccatcac caaggatttt ggcaactcac    240
ctccactatg acaaattacc tgggtctatc ttcgagaata aagccaagag acagcatctc    300
actatgttgc ccaggctggt ctcgaactcc tga                                 333
```

<210> SEQ ID NO 4
<211> LENGTH: 110
<212> TYPE: PRT
<213> ORGANISM: homo sapiens

<400> SEQUENCE: 4

```
Met Cys Thr Ser Glu Thr Phe Gln Ala Leu Asp Thr Phe Glu Ala Arg
 1               5                  10                  15

His Asp Asp Ile Val Leu Ala Ser Tyr Pro Lys Cys Gly Ser Asn Trp
            20                  25                  30

Ile Leu His Ile Val Ser Glu Leu Ile Tyr Ala Val Ser Lys Lys Lys
        35                  40                  45

Tyr Lys Tyr Pro Glu Phe Pro Val Leu Glu Cys Gly Asp Ser Glu Lys
 50                  55                  60

Tyr Gln Arg Met Lys Gly Phe Pro Ser Pro Arg Ile Leu Ala Thr His
 65                  70                  75                  80

Leu His Tyr Asp Lys Leu Pro Gly Ser Ile Phe Glu Asn Lys Ala Lys
                85                  90                  95

Arg Gln His Leu Thr Met Leu Pro Arg Leu Val Ser Asn Ser
            100                 105                 110
```

<210> SEQ ID NO 5
<211> LENGTH: 798
<212> TYPE: DNA
<213> ORGANISM: homo sapiens

<400> SEQUENCE: 5

```
atgtgcacct cagaaacttt ccaagcgctg gacaccttcg aagccagaca tgatgacatc     60
gtgctagcat cttatccaaa gtgcggttca aactggattc tccacattgt cagtgaatta    120
atatatgctg tttctaaaaa aaagtataaa tatccagaat tcccagttct tgaatgtggg    180
gattcagaaa aatatcagag aatgaaaggc tttccatcac caaggatttt ggcaactcac    240
ctccactatg acaaattacc tgggtctatc ttcgagaata aagccaagat attggtgata    300
tttcgaaacc ctaaagatac agcagtatct tttttgcatt tccacaacga tgtccccgat    360
attccaagct atggctcttg ggatgaattc ttcagacagt tcatgaaagg acaagtttct    420
tggggaaggt attttgattt tgcaatcaat tggaacaaac atcttgatgg cgacaatgtt    480
aagttcatat tatatgaaga cctgaaagag aatctggctg ctggaataaa acagattgct    540
gagttcttgg gattctttct aactggggag caaattcaaa ctatctcagt ccagagcacc    600
ttccaagcca tgcgtgcgaa gtctcaggac acacacggtg ctgtcggccc attccttttc    660
cgcaaaggtg aagttggtga ttggaaaaat ttgttcagtg aaattcagaa ccaggaaatg    720
gatgaaaaat tcaaagagtg cttagcaggc acctccctcg gagcaaagtt gaagtatgaa    780
tcatattgcc agggttga                                                  798
```

<210> SEQ ID NO 6
<211> LENGTH: 265
<212> TYPE: PRT
<213> ORGANISM: homo sapiens

<400> SEQUENCE: 6

```
Met Cys Thr Ser Glu Thr Phe Gln Ala Leu Asp Thr Phe Glu Ala Arg
 1               5                  10                  15
His Asp Asp Ile Val Leu Ala Ser Tyr Pro Lys Cys Gly Ser Asn Trp
             20                  25                  30
Ile Leu His Ile Val Ser Glu Leu Ile Tyr Ala Val Ser Lys Lys Lys
         35                  40                  45
Tyr Lys Tyr Pro Glu Phe Pro Val Leu Glu Cys Gly Asp Ser Glu Lys
 50                  55                  60
Tyr Gln Arg Met Lys Gly Phe Pro Ser Pro Arg Ile Leu Ala Thr His
 65                  70                  75                  80
Leu His Tyr Asp Lys Leu Pro Gly Ser Ile Phe Glu Asn Lys Ala Lys
                 85                  90                  95
Ile Leu Val Ile Phe Arg Asn Pro Lys Asp Thr Ala Val Ser Phe Leu
            100                 105                 110
His Phe His Asn Asp Val Pro Asp Ile Pro Ser Tyr Gly Ser Trp Asp
        115                 120                 125
Glu Phe Phe Arg Gln Phe Met Lys Gly Gln Val Ser Trp Gly Arg Tyr
130                 135                 140
Phe Asp Phe Ala Ile Asn Trp Asn Lys His Leu Asp Gly Asp Asn Val
145                 150                 155                 160
Lys Phe Ile Leu Tyr Glu Asp Leu Lys Glu Asn Leu Ala Ala Gly Ile
                165                 170                 175
Lys Gln Ile Ala Glu Phe Leu Gly Phe Phe Leu Thr Gly Glu Gln Ile
            180                 185                 190
Gln Thr Ile Ser Val Gln Ser Thr Phe Gln Ala Met Arg Ala Lys Ser
        195                 200                 205
Gln Asp Thr His Gly Ala Val Gly Pro Phe Leu Phe Arg Lys Gly Glu
    210                 215                 220
Val Gly Asp Trp Lys Asn Leu Phe Ser Glu Ile Gln Asn Gln Glu Met
225                 230                 235                 240
Asp Glu Lys Phe Lys Glu Cys Leu Ala Gly Thr Ser Leu Gly Ala Lys
                245                 250                 255
Leu Lys Tyr Glu Ser Tyr Cys Gln Gly
            260                 265
```

<210> SEQ ID NO 7
<211> LENGTH: 447
<212> TYPE: DNA
<213> ORGANISM: homo sapiens

<400> SEQUENCE: 7

```
atgtgcacct cagaaacttt ccaagcgctg gacaccttcg aagccagaca tgatgacatc      60
gtgctagcat cttatccaaa gtgcggttca aactggattc tccacattgt cagtgaatta     120
atatatgctg tttctaaaaa aaagtataaa tatccagaat tcccagttct tgaatgtggg     180
gattcagaaa aatatcagag aatgaaaggc tttccatcac caaggatttt ggcaactcac     240
ctccactatg acaaattacc tgggtctatc ttcgagaata agccaagat  attggtgata     300
tttcgaaacc ctaagataca gcagtatct ttttttgcatt ccacaacga  tgtccccgat     360
attccaagct atggctcttg ggatgaattc ttcagacagt tcatgaaagg acaagaatct     420
ggctgctgga ataaaacaga ttgctga                                         447
```

<210> SEQ ID NO 8
<211> LENGTH: 148
<212> TYPE: PRT
<213> ORGANISM: homo sapiens

<400> SEQUENCE: 8

```
Met Cys Thr Ser Glu Thr Phe Gln Ala Leu Asp Thr Phe Glu Ala Arg
  1               5                  10                  15

His Asp Asp Ile Val Leu Ala Ser Tyr Pro Lys Cys Gly Ser Asn Trp
             20                  25                  30

Ile Leu His Ile Val Ser Glu Leu Ile Tyr Ala Val Ser Lys Lys Lys
         35                  40                  45

Tyr Lys Tyr Pro Glu Phe Pro Val Leu Glu Cys Gly Asp Ser Glu Lys
     50                  55                  60

Tyr Gln Arg Met Lys Gly Phe Pro Ser Pro Arg Ile Leu Ala Thr His
 65                  70                  75                  80

Leu His Tyr Asp Lys Leu Pro Gly Ser Ile Phe Glu Asn Lys Ala Lys
                 85                  90                  95

Ile Leu Val Ile Phe Arg Asn Pro Lys Asp Thr Ala Val Ser Phe Leu
            100                 105                 110

His Phe His Asn Asp Val Pro Asp Ile Pro Ser Tyr Gly Ser Trp Asp
        115                 120                 125

Glu Phe Phe Arg Gln Phe Met Lys Gly Gln Ser Gly Cys Trp Asn
    130                 135                 140

Lys Thr Asp Cys
145
```

<210> SEQ ID NO 9
<211> LENGTH: 447
<212> TYPE: DNA
<213> ORGANISM: homo sapiens

<400> SEQUENCE: 9

```
atggctgata atccaaatt tattgaatac attgacgaag ctttagaaaa atcaaaagaa      60
actgcactct ctcatttatt tttcacctat caggggattc cttaccccat caccatgtgc    120
acctcagaaa ctttccaagc gctggacacc ttcgaagcca gacatgatga catcgtgcta    180
gcatcttatc caaagtgcgg ttcaaactgg attctccaca ttgtcagtga attaatatat    240
gctgtttcta aaaaaaagta taaatatcca gaattcccag ttcttgaatg tggggattca    300
gaaaaatatc agagaatgaa aggctttcca tcaccaagga ttttggcaac tcacctccac    360
tatgacaaat acctgggtc tatcttcgag aataaagcca agagacagca tctcactatg    420
ttgcccaggc tggtctcgaa ctcctga                                        447
```

<210> SEQ ID NO 10
<211> LENGTH: 148
<212> TYPE: PRT
<213> ORGANISM: homo sapiens

<400> SEQUENCE: 10

```
Met Ala Asp Lys Ser Lys Phe Ile Glu Tyr Ile Asp Glu Ala Leu Glu
  1               5                  10                  15

Lys Ser Lys Glu Thr Ala Leu Ser His Leu Phe Phe Thr Tyr Gln Gly
             20                  25                  30

Ile Pro Tyr Pro Ile Thr Met Cys Thr Ser Glu Thr Phe Gln Ala Leu
         35                  40                  45

Asp Thr Phe Glu Ala Arg His Asp Asp Ile Val Leu Ala Ser Tyr Pro
```

```
                50                  55                  60
Lys Cys Gly Ser Asn Trp Ile Leu His Ile Val Ser Glu Leu Ile Tyr
 65                  70                  75                  80

Ala Val Ser Lys Lys Lys Tyr Lys Tyr Pro Glu Phe Pro Val Leu Glu
                 85                  90                  95

Cys Gly Asp Ser Glu Lys Tyr Gln Arg Met Lys Gly Phe Pro Ser Pro
                100                 105                 110

Arg Ile Leu Ala Thr His Leu His Tyr Asp Lys Leu Pro Gly Ser Ile
            115                 120                 125

Phe Glu Asn Lys Ala Lys Arg Gln His Leu Thr Met Leu Pro Arg Leu
        130                 135                 140

Val Ser Asn Ser
145

<210> SEQ ID NO 11
<211> LENGTH: 561
<212> TYPE: DNA
<213> ORGANISM: homo sapiens

<400> SEQUENCE: 11
atggctgata aatccaaatt tattgaatac attgacgaag ctttagaaaa atcaaaagaa      60
actgcactct ctcatttatt tttcacctat caggggattc cttaccccat caccatgtgc     120
acctcagaaa ctttccaagc gctggacacc ttcgaagcca gacatgatga catcgtgcta     180
gcatcttatc caaagtgcgg ttcaaactgg attctccaca ttgtcagtga attaatatat     240
gctgtttcta aaaaaagta taaatatcca gaattcccag ttcttgaatg tggggattca     300
gaaaaatatc agagaatgaa aggctttcca tcaccaagga ttttggcaac tcacctccac     360
tatgacaaat acctgggtc tatcttcgag aataaagcca agatattggt gatatttcga     420
aaccctaaag atacagcagt atcttttttg catttccaca acgatgtccc cgatattcca     480
agctatggct cttgggatga attcttcaga cagttcatga aggacaaga atctggctgc     540 tggaataaaa cagattgctg a                                              561

<210> SEQ ID NO 12
<211> LENGTH: 186
<212> TYPE: PRT
<213> ORGANISM: homo sapiens

<400> SEQUENCE: 12

Met Ala Asp Lys Ser Lys Phe Ile Glu Tyr Ile Asp Glu Ala Leu Glu
 1               5                  10                  15

Lys Ser Lys Glu Thr Ala Leu Ser His Leu Phe Phe Thr Tyr Gln Gly
                20                  25                  30

Ile Pro Tyr Pro Ile Thr Met Cys Thr Ser Glu Thr Phe Gln Ala Leu
            35                  40                  45

Asp Thr Phe Glu Ala Arg His Asp Asp Ile Val Leu Ala Ser Tyr Pro
        50                  55                  60

Lys Cys Gly Ser Asn Trp Ile Leu His Ile Val Ser Glu Leu Ile Tyr
 65                  70                  75                  80

Ala Val Ser Lys Lys Lys Tyr Lys Tyr Pro Glu Phe Pro Val Leu Glu
                 85                  90                  95

Cys Gly Asp Ser Glu Lys Tyr Gln Arg Met Lys Gly Phe Pro Ser Pro
                100                 105                 110

Arg Ile Leu Ala Thr His Leu His Tyr Asp Lys Leu Pro Gly Ser Ile
            115                 120                 125
```

```
Phe Glu Asn Lys Ala Lys Ile Leu Val Ile Phe Arg Asn Pro Lys Asp
        130                 135                 140

Thr Ala Val Ser Phe Leu His Phe His Asn Asp Val Pro Asp Ile Pro
145                 150                 155                 160

Ser Tyr Gly Ser Trp Asp Glu Phe Phe Arg Gln Phe Met Lys Gly Gln
                165                 170                 175

Glu Ser Gly Cys Trp Asn Lys Thr Asp Cys
            180                 185

<210> SEQ ID NO 13
<211> LENGTH: 180
<212> TYPE: DNA
<213> ORGANISM: homo sapiens

<400> SEQUENCE: 13
atgcacacac gtgcacattt tcacctttt  gtgtatattt ttaagagaat gaaaggcttt      60
ccatcaccaa ggattttggc aactcacctc cactatgaca aattacctgg gtctatcttc     120
gagaataaag ccaagagaca gcatctcact atgttgccca ggctggtctc gaactcctga    180

<210> SEQ ID NO 14
<211> LENGTH: 59
<212> TYPE: PRT
<213> ORGANISM: homo sapiens

<400> SEQUENCE: 14

Met His Thr Arg Ala His Phe His Leu Phe Val Tyr Ile Phe Lys Arg
1               5                   10                  15

Met Lys Gly Phe Pro Ser Pro Arg Ile Leu Ala Thr His Leu His Tyr
            20                  25                  30

Asp Lys Leu Pro Gly Ser Ile Phe Glu Asn Lys Ala Lys Arg Gln His
        35                  40                  45

Leu Thr Met Leu Pro Arg Leu Val Ser Asn Ser
    50                  55

<210> SEQ ID NO 15
<211> LENGTH: 645
<212> TYPE: DNA
<213> ORGANISM: homo sapiens

<400> SEQUENCE: 15
atgcacacac gtgcacattt tcacctttt  gtgtatattt ttaagagaat gaaaggcttt      60
ccatcaccaa ggattttggc aactcacctc cactatgaca aattacctgg gtctatcttc     120
gagaataaag ccaagatatt ggtgatattt cgaaacccta agatacagc agtatctttt     180 ttgcatttcc acaacgatgt ccccgatatt ccaagctatg gctcttggga tgaattcttc     240
agacagttca tgaaaggaca gtttcttgg ggaaggtatt ttgattttgc aatcaattgg      300
aacaaacatc ttgatggcga caatgttaag ttcatattat atgaagacct gaaagagaat     360
ctggctgctg aataaaaaca gattgctgag ttcttgggat tctttctaac tggggagcaa    420
attcaaacta tctcagtcca gagcaccttc caagccatgc gtgcgaagtc tcaggacaca    480
cacggtgctg tcggcccatt ccttttccgc aaaggtgaag ttggtgattg aaaaatttg     540 ttcagtgaaa ttcagaacca ggaaatggat gaaaaattca agagtgcttt agcaggcacc    600
tccctcggag caaagttgaa gtatgaatca tattgccagg gttga                    645

<210> SEQ ID NO 16
```

-continued

<211> LENGTH: 214
<212> TYPE: PRT
<213> ORGANISM: homo sapiens

<400> SEQUENCE: 16

Met His Thr Arg Ala His Phe His Leu Phe Val Tyr Ile Phe Lys Arg
1               5                   10                  15

Met Lys Gly Phe Pro Ser Pro Arg Ile Leu Ala Thr His Leu His Tyr
            20                  25                  30

Asp Lys Leu Pro Gly Ser Ile Phe Glu Asn Lys Ala Lys Ile Leu Val
        35                  40                  45

Ile Phe Arg Asn Pro Lys Asp Thr Ala Val Ser Phe Leu His Phe His
    50                  55                  60

Asn Asp Val Pro Asp Ile Pro Ser Tyr Gly Ser Trp Asp Glu Phe Phe
65                  70                  75                  80

Arg Gln Phe Met Lys Gly Gln Val Ser Trp Gly Arg Tyr Phe Asp Phe
                85                  90                  95

Ala Ile Asn Trp Asn Lys His Leu Asp Gly Asp Asn Val Lys Phe Ile
            100                 105                 110

Leu Tyr Glu Asp Leu Lys Glu Asn Leu Ala Ala Gly Ile Lys Gln Ile
        115                 120                 125

Ala Glu Phe Leu Gly Phe Phe Leu Thr Gly Gln Ile Gln Thr Ile
    130                 135                 140

Ser Val Gln Ser Thr Phe Gln Ala Met Arg Ala Lys Ser Gln Asp Thr
145                 150                 155                 160

His Gly Ala Val Gly Pro Phe Leu Phe Arg Lys Gly Glu Val Gly Asp
                165                 170                 175

Trp Lys Asn Leu Phe Ser Glu Ile Gln Asn Gln Glu Met Asp Glu Lys
            180                 185                 190

Phe Lys Glu Cys Leu Ala Gly Thr Ser Leu Gly Ala Lys Leu Lys Tyr
        195                 200                 205

Glu Ser Tyr Cys Gln Gly
    210

<210> SEQ ID NO 17
<211> LENGTH: 294
<212> TYPE: DNA
<213> ORGANISM: homo sapiens

<400> SEQUENCE: 17
atgcacacac gtgcacattt tcaccttttt gtgtatattt ttaagagaat gaaaggcttt      60
ccatcaccaa ggattttggc aactcacctc cactatgaca aattacctgg gtctatcttc     120
gagaataaag ccaagatatt ggtgatattt cgaaacccta agatacagc agtatctttt      180 ttgcatttcc acaacgatgt ccccgatatt ccaagctatg gctcttggga tgaattcttc     240
agacagttca tgaaggaca agaatctggc tgctggaata aaacagattg ctga            294

<210> SEQ ID NO 18
<211> LENGTH: 97
<212> TYPE: PRT
<213> ORGANISM: homo sapiens

<400> SEQUENCE: 18

Met His Thr Arg Ala His Phe His Leu Phe Val Tyr Ile Phe Lys Arg
1               5                   10                  15

Met Lys Gly Phe Pro Ser Pro Arg Ile Leu Ala Thr His Leu His Tyr
            20                  25                  30

-continued

Asp Lys Leu Pro Gly Ser Ile Phe Glu Asn Lys Ala Lys Ile Leu Val
           35                   40                  45

Ile Phe Arg Asn Pro Lys Asp Thr Ala Val Ser Phe Leu His Phe His
    50                  55                  60

Asn Asp Val Pro Asp Ile Pro Ser Tyr Gly Ser Trp Asp Glu Phe Phe
65                  70                  75                  80

Arg Gln Phe Met Lys Gly Gln Glu Ser Gly Cys Trp Asn Lys Thr Asp
                85                  90                  95

Cys

<210> SEQ ID NO 19
<211> LENGTH: 2153
<212> TYPE: DNA
<213> ORGANISM: homo sapiens

<400> SEQUENCE: 19

| | | | | | |
|---|---|---|---|---|---|
| ggagaaagca | agaggcttac | actgcccaca | atcgcagtta | gtaaaatcag | aattcacatt | 60 |
| taaacccagg | aaactgacta | cgtgtagcct | gttctgggtc | gttttttctaa | caccctgaaa | 120 |
| cttaaagtgt | gatagtctca | gaggactacc | aacataagca | tcacctgaaa | acttgttaga | 180 |
| aatgaagaac | taggccgggc | gcggtggctc | acgcctataa | tcccagcact | ttggaggcc | 240 |
| tagatgggag | gatcacgaca | tcaggagacc | gagaccatcc | tggctaacac | gtgaaaaatg | 300 |
| ccatggcctt | gtttctcata | gcaggtaaag | aagaaccaaa | gaattcactg | gtactaacaa | 360 |
| ttaaacctat | gccctctgag | atctcattag | tgagggaggg | gtggatgaga | attaaatgat | 420 |
| ttcttttttca | tgtgactggg | aggagcccctt | tattccagcc | cctgcccaac | tccattaaaa | 480 |
| gcaatcactc | ccctgaaca | gccacagagc | aggttctttt | acaggagcc | accatggctg | 540 |
| ataaatccaa | atttattgaa | tacattgacg | aagctttaga | aaaatcaaaa | gaaactgcac | 600 |
| tctctcattt | attttttcacc | tatcagggga | ttccttaccc | catcaccatg | tgcacctcag | 660 |
| aaactttcca | agcgctggac | accttcgaag | ccagacatga | tgacatcgtg | ctagcatctt | 720 |
| atccaaagtg | cggttcaaac | tggattctcc | acattgtcag | tgaattaata | tatgctgttt | 780 |
| ctaaaaaaaa | gtataaatat | ccagaattcc | cagttcttga | atgtgggat | tcagaaaaat | 840 |
| atctagtgac | agtagtgcta | gaaactatca | cttagatacc | aaacctagga | gtgattcaac | 900 |
| acacacacac | acatgcacac | acgtgcacat | tttcacctttt | ttgtgtatat | ttttaagaga | 960 |
| atgaaaggct | ttccatcacc | aaggattttg | gcaactcacc | tccactatga | caaattacct | 1020 |
| gggtctatct | tcgagaataa | agccaagaga | cagcatctca | ctatgttgcc | caggctggtc | 1080 |
| tcgaactcct | gacttcaaga | gatccttctg | ccaccaaggc | ctcccaaagt | gatattggtg | 1140 |
| atatttcgaa | accctaaaga | tacagcagta | tctttttttgc | atttccacaa | cgatgtcccc | 1200 |
| gatattccaa | gctatggctc | ttgggatgaa | ttcttcagac | agttcatgaa | aggcaagtt | 1260 |
| tcttggggaa | ggtattttga | ttttgcaatc | aattggaaca | aacatcttga | tggcgacaat | 1320 |
| gttaagttca | tattatatga | agacctgaaa | gagaatctgg | ctgctggaat | aaaacagatt | 1380 |
| gctgagttct | tgggattctt | tctaactggg | gagcaaattc | aaactatctc | agtccagagc | 1440 |
| accttccaag | ccatgcgtgc | gaagtctcag | gacacacacg | tgctgtcgg | cccattcctt | 1500 |
| ttccgcaaag | gtgaagttgg | tgattggaaa | atttgttca | gtgaaattca | gaaccaggaa | 1560 |
| atggatgaaa | aattcaaaga | gtgcttagca | ggcacctccc | tcggagcaaa | gttgaagtat | 1620 |
| gaatcatatt | gccagggttg | attccagtca | attcagcagg | cctagattta | ttttcccttaa | 1680 |

```
taataattaa gtgtaaataa ttaaatgata attcaatcaa ataatcaaat aataattaaa      1740
caatattgaa atctaaataa tacaatacaa aataataata caatttaata ataatgataa      1800
catcggacat ttttgagcac aaatataagt ttgttcactt tttcaagaaa ggatatttca      1860
gcagtcccaa agggacacta ttattaatac atcacactgg agttttaact tatttttgtgc     1920 tctaggttca cgtaagaggg taaggagata ctatcagaga catacctaaa gctgtgtttg      1980
gccatagatg acacaggcct ccaaatggtg cacaattttc tgtactttgc tcgtaatata      2040
actcctttct tactatggat aaaagcactt ggggtggcta tctcagacaa tgttggggga     2100
gagttaattc caactctgca ataaattcca ttctaatttg gttcaggaaa aaa            2153

<210> SEQ ID NO 20
<211> LENGTH: 432
<212> TYPE: DNA
<213> ORGANISM: homo sapiens

<400> SEQUENCE: 20
atgaccgatg ctgagagagt ggatcaggca taccgagaaa atggatttaa catctacgtc        60
agtgataaaa tctccttgaa tcgctctctc ccagatatcc ggcacccaaa ctgcaacagc       120
aagcgctacc tggagacact tcccaacaca agcatcatca tccccttcca caacgagggc       180
tggtcctccc tcctccgcac cgtccacagt gtgctcaatc gctcgcctcc agagctggtc       240
gccgagattg tactggtcga cgacttcagt gatcgaggta ggatccgtcc cacccagcct       300 cccacccctct gtgcttcatc tggcgactca ccaaagggat ggcagttttt cccttcttta       360
gcagcatcaa catataggcc atcattggct aaatgcctgg acgttgcact gtgcacacat       420
tttctcattt aa                                                          432

<210> SEQ ID NO 21
<211> LENGTH: 143
<212> TYPE: PRT
<213> ORGANISM: homo sapiens

<400> SEQUENCE: 21

Met Thr Asp Ala Glu Arg Val Asp Gln Ala Tyr Arg Glu Asn Gly Phe
  1               5                  10                  15

Asn Ile Tyr Val Ser Asp Lys Ile Ser Leu Asn Arg Ser Leu Pro Asp
                 20                  25                  30

Ile Arg His Pro Asn Cys Asn Ser Lys Arg Tyr Leu Glu Thr Leu Pro
             35                  40                  45

Asn Thr Ser Ile Ile Ile Pro Phe His Asn Glu Gly Trp Ser Ser Leu
         50                  55                  60

Leu Arg Thr Val His Ser Val Leu Asn Arg Ser Pro Pro Glu Leu Val
 65                  70                  75                  80

Ala Glu Ile Val Leu Val Asp Asp Phe Ser Asp Arg Gly Arg Ile Arg
                 85                  90                  95

Pro Thr Gln Pro Pro Thr Leu Cys Ala Ser Gly Asp Ser Pro Lys
                100                 105                 110

Gly Trp Gln Val Phe Pro Ser Leu Ala Ala Ser Thr Tyr Arg Pro Ser
            115                 120                 125

Leu Ala Lys Cys Leu Asp Val Ala Leu Cys Thr His Phe Leu Ile
        130                 135                 140

<210> SEQ ID NO 22
<211> LENGTH: 675
<212> TYPE: DNA
```

<213> ORGANISM: homo sapiens

<400> SEQUENCE: 22

```
atgaccgatg ctgagagagt ggatcaggca taccgagaaa atggatttaa catctacgtc    60
agtgataaaa tctccttgaa tcgctctctc ccagatatcc ggcacccaaa ctgcaacagc   120
aagcgctacc tggagacact tcccaacaca agcatcatca tccccttcca caacgagggc   180
tggtcctccc tcctccgcac cgtccacagt gtgctcaatc gctcgcctcc agagctggtc   240
gccgagattg tactggtcga cgacttcagt gatcgagagc acctgaagaa gcctcttgaa   300
gactacatgg cccttttccc cagtgtgagg attcttcgaa ccaagaaacg ggaagggctg   360
ataaggaccc gaatgctggg ggcctcagtg caactgggg atgtcatcac attcttggat   420
tcacactgtg aagccaatgt caactggctt ccccccttgc ttggtaaggg agcccctccc   480
acttggaggg aggcaaactg caatgagcca gtgccagtgg cccccctcctg ctgcagggag   540
ccatccataa gccttccctt gcctgttcaa gatgccccca gcacaatgcc aggtgccatg   600
agggattcag aagttcagga gtgctcaaaa ttaaaatcca gccagtcctg tcccttcatt   660
tcacagagaa gttaa                                                   675
```

<210> SEQ ID NO 23
<211> LENGTH: 224
<212> TYPE: PRT
<213> ORGANISM: homo sapiens

<400> SEQUENCE: 23

```
Met Thr Asp Ala Glu Arg Val Asp Gln Ala Tyr Arg Glu Asn Gly Phe
 1               5                  10                  15

Asn Ile Tyr Val Ser Asp Lys Ile Ser Leu Asn Arg Ser Leu Pro Asp
            20                  25                  30

Ile Arg His Pro Asn Cys Asn Ser Lys Arg Tyr Leu Glu Thr Leu Pro
        35                  40                  45

Asn Thr Ser Ile Ile Ile Pro Phe His Asn Glu Gly Trp Ser Ser Leu
    50                  55                  60

Leu Arg Thr Val His Ser Val Leu Asn Arg Ser Pro Pro Glu Leu Val
65                  70                  75                  80

Ala Glu Ile Val Leu Val Asp Asp Phe Ser Asp Arg Glu His Leu Lys
                85                  90                  95

Lys Pro Leu Glu Asp Tyr Met Ala Leu Phe Pro Ser Val Arg Ile Leu
            100                 105                 110

Arg Thr Lys Lys Arg Glu Gly Leu Ile Arg Thr Arg Met Leu Gly Ala
        115                 120                 125

Ser Val Ala Thr Gly Asp Val Ile Thr Phe Leu Asp Ser His Cys Glu
    130                 135                 140

Ala Asn Val Asn Trp Leu Pro Pro Leu Leu Gly Lys Gly Ala Pro Pro
145                 150                 155                 160

Thr Trp Arg Glu Ala Asn Cys Asn Glu Pro Val Pro Val Ala Pro Ser
                165                 170                 175

Cys Cys Arg Glu Pro Ser Ile Ser Leu Pro Leu Pro Val Gln Asp Ala
            180                 185                 190

Pro Ser Thr Met Pro Gly Ala Met Arg Asp Ser Glu Val Gln Glu Cys
        195                 200                 205

Ser Lys Leu Lys Ser Ser Gln Ser Cys Pro Phe Ile Ser Gln Arg Ser
    210                 215                 220
```

-continued

<210> SEQ ID NO 24
<211> LENGTH: 339
<212> TYPE: DNA
<213> ORGANISM: homo sapiens

<400> SEQUENCE: 24

| | | | | | |
|---|---|---|---|---|---|
| atgaccgatg | ctgagagagt | ggatcaggca | taccgagaaa | atggatttaa | catctacgtc | 60 |
| agtgataaaa | tctccttgaa | tcgctctctc | ccagatatcc | ggcacccaaa | ctgcaacagc | 120 |
| aagcgctacc | tggagacact | tcccaacaca | agcatcatca | tccccttcca | caacgagggc | 180 |
| tggtcctccc | tcctccgcac | cgtccacagt | gtgctcaatc | gctcgcctcc | agagctggtc | 240 |
| gccgagattg | tactggtcga | cgacttcagt | gatcgaggca | tctcttggct | tcttcagacc | 300 |
| gcattgctcg | gaaccgcaag | accattgtgt | gcccgatga | | | 339 |

<210> SEQ ID NO 25
<211> LENGTH: 112
<212> TYPE: PRT
<213> ORGANISM: homo sapiens

<400> SEQUENCE: 25

Met Thr Asp Ala Glu Arg Val Asp Gln Ala Tyr Arg Glu Asn Gly Phe
 1               5                  10                  15

Asn Ile Tyr Val Ser Asp Lys Ile Ser Leu Asn Arg Ser Leu Pro Asp
            20                  25                  30

Ile Arg His Pro Asn Cys Asn Ser Lys Arg Tyr Leu Glu Thr Leu Pro
        35                  40                  45

Asn Thr Ser Ile Ile Ile Pro Phe His Asn Glu Gly Trp Ser Ser Leu
    50                  55                  60

Leu Arg Thr Val His Ser Val Leu Asn Arg Ser Pro Pro Glu Leu Val
65                  70                  75                  80

Ala Glu Ile Val Leu Val Asp Asp Phe Ser Asp Arg Gly Ile Ser Trp
                85                  90                  95

Leu Leu Gln Thr Ala Leu Leu Gly Thr Ala Arg Pro Leu Cys Ala Arg
            100                 105                 110

<210> SEQ ID NO 26
<211> LENGTH: 810
<212> TYPE: DNA
<213> ORGANISM: homo sapiens

<400> SEQUENCE: 26

| | | | | | |
|---|---|---|---|---|---|
| atgaccgatg | ctgagagagt | ggatcaggca | taccgagaaa | atggatttaa | catctacgtc | 60 |
| agtgataaaa | tctccttgaa | tcgctctctc | ccagatatcc | ggcacccaaa | ctgcaacagc | 120 |
| aagcgctacc | tggagacact | tcccaacaca | agcatcatca | tccccttcca | caacgagggc | 180 |
| tggtcctccc | tcctccgcac | cgtccacagt | gtgctcaatc | gctcgcctcc | agagctggtc | 240 |
| gccgagattg | tactggtcga | cgacttcagt | gatcgagagc | acctgaagaa | gcctcttgaa | 300 |
| gactacatgg | cccttttccc | cagtgtgagg | attcttcgaa | ccaagaaacg | ggaagggctg | 360 |
| ataaggaccc | gaatgctggg | ggcctcagtg | gcaactgggg | atgtcatcac | attcttggat | 420 |
| tcacactgtg | aagccaatgt | caactggctt | ccccccttgc | ttgaccgcat | tgctcggaac | 480 |
| cgcaagacca | ttgtgtgccc | gatgattgat | gtaattgacc | atgacgactt | tcggtacgag | 540 |
| acacaggcag | gggatgccat | gcggggagcc | tttgactggg | agatgtacta | caagcggatc | 600 |
| ccgatccctc | cagaactgca | gaaagctgac | cccagcgacc | catttgagtc | tcccgtgatg | 660 |
| gccggtggac | tgttcgccgt | ggatcggaag | tggttctggg | aactcggcgg | gtatgaccca | 720 |

```
ggcttggaga tctggggagg ggagcagtat gaaatctcct tcaaggtgag ccagctctcc    780
agacgccccg ttcttggcac agcctcctga                                     810
```

<210> SEQ ID NO 27
<211> LENGTH: 269
<212> TYPE: PRT
<213> ORGANISM: homo sapiens

<400> SEQUENCE: 27

```
Met Thr Asp Ala Glu Arg Val Asp Gln Ala Tyr Arg Glu Asn Gly Phe
 1               5                  10                  15

Asn Ile Tyr Val Ser Asp Lys Ile Ser Leu Asn Arg Ser Leu Pro Asp
            20                  25                  30

Ile Arg His Pro Asn Cys Asn Ser Lys Arg Tyr Leu Glu Thr Leu Pro
        35                  40                  45

Asn Thr Ser Ile Ile Ile Pro Phe His Asn Glu Gly Trp Ser Ser Leu
    50                  55                  60

Leu Arg Thr Val His Ser Val Leu Asn Arg Ser Pro Pro Glu Leu Val
65                  70                  75                  80

Ala Glu Ile Val Leu Val Asp Asp Phe Ser Asp Arg Glu His Leu Lys
                85                  90                  95

Lys Pro Leu Glu Asp Tyr Met Ala Leu Phe Pro Ser Val Arg Ile Leu
            100                 105                 110

Arg Thr Lys Lys Arg Glu Gly Leu Ile Arg Thr Arg Met Leu Gly Ala
        115                 120                 125

Ser Val Ala Thr Gly Asp Val Ile Thr Phe Leu Asp Ser His Cys Glu
    130                 135                 140

Ala Asn Val Asn Trp Leu Pro Pro Leu Leu Asp Arg Ile Ala Arg Asn
145                 150                 155                 160

Arg Lys Thr Ile Val Cys Pro Met Ile Asp Val Ile Asp His Asp Asp
                165                 170                 175

Phe Arg Tyr Glu Thr Gln Ala Gly Asp Ala Met Arg Gly Ala Phe Asp
            180                 185                 190

Trp Glu Met Tyr Tyr Lys Arg Ile Pro Ile Pro Pro Glu Leu Gln Lys
        195                 200                 205

Ala Asp Pro Ser Asp Pro Phe Glu Ser Pro Val Met Ala Gly Gly Leu
    210                 215                 220

Phe Ala Val Asp Arg Lys Trp Phe Trp Glu Leu Gly Gly Tyr Asp Pro
225                 230                 235                 240

Gly Leu Glu Ile Trp Gly Gly Glu Gln Tyr Glu Ile Ser Phe Lys Val
                245                 250                 255

Ser Gln Leu Ser Arg Arg Pro Val Leu Gly Thr Ala Ser
            260                 265
```

<210> SEQ ID NO 28
<211> LENGTH: 1608
<212> TYPE: DNA
<213> ORGANISM: homo sapiens

<400> SEQUENCE: 28

```
atgaccgatg ctgagagagt ggatcaggca taccgagaaa atggatttaa catctacgtc    60
agtgataaaa tctccttgaa tcgctctctc ccagatatcc ggcacccaaa ctgcaacagc   120
aagcgctacc tggagacact tcccaacaca agcatcatca tccccttcca caacgagggc   180
tggtcctccc tcctccgcac cgtccacagt gtgctcaatc gctcgcctcc agagctggtc   240
```

```
gccgagattg tactggtcga cgacttcagt gatcgagagc acctgaagaa gcctcttgaa    300
gactacatgg ccctttccc cagtgtgagg attcttcgaa ccaagaaacg ggaagggctg    360
ataaggaccc gaatgctggg ggcctcagtg gcaactgggg atgtcatcac attcttggat    420
tcacactgtg aagccaatgt caactggctt ccccccttgc ttgaccgcat tgctcggaac    480
cgcaagacca ttgtgtgccc gatgattgat gtaattgacc atgacgactt tcggtacgag    540
acacaggcag gggatgccat gcggggagcc tttgactggg agatgtacta caagcggatc    600
ccgatccctc cagaactgca gaaagctgac cccagcgacc catttgagtc tcccgtgatg    660
gccggtggac tgttcgccgt ggatcggaag tggttctggg aactcggcgg gtatgaccca    720
ggcttggaga tctggggagg ggagcagtat gaaatctcct tcaagggtct ccatatgttg    780
cccaggctgg tctcaaactc ctggcctcaa gcagtcttcc tgcctcgggc tcccaacatg    840
ctggcattac aggtgtggat gtgtgggggc cgcatggagg acatccctg ctccagggtg    900
ggccatatct acaggaagta tgtgccctac aaggtcccgg ccggagtcag cctggcccgg    960
aaccttaagc gggtggccga agtgtggatg gatgagtacg cagagtacat ttaccagcgc   1020
cggcctgaat accgccacct ctccgctggg gatgtcgcag tccagaaaaa gctccgcagc   1080
tcccttaact gcaagagttt caagtggttt atgacgaaga tagcctggga cctgcccaaa   1140
ttctacccac ccgtggagcc cccggctgca gcttgggggg agatccgaaa tgtgggcaca   1200
gggctgtgtg cagacacaaa gcacgggggcc ttgggctccc cactaaggct agagggctgc   1260
gtccgaggcc gtggggaggc tgcctggaac aacatgcagg tattcacctt cacctggaga   1320
gaggacatcc ggcctggaga ccccccagcac accaagaagt tctgctttga tgccatttcc   1380
cacaccagcc ctgtcacgct gtacgactgc acacagcatga agggcaacca gctgtggaaa   1440
taccgcaaag acaagaccct gtaccaccct gtcagtggca gctgcatgga ctgcagtgaa   1500
agtgaccata ggatcttcat gaacacctgc aacccatcct ctctcaccca gcagtggctg   1560
tttgaacaca ccaactcaac agtcttggaa aaattcaata ggaactga                1608
```

<210> SEQ ID NO 29
<211> LENGTH: 535
<212> TYPE: PRT
<213> ORGANISM: homo sapiens

<400> SEQUENCE: 29

```
Met Thr Asp Ala Glu Arg Val Asp Gln Ala Tyr Arg Glu Asn Gly Phe
1               5                   10                  15

Asn Ile Tyr Val Ser Asp Lys Ile Ser Leu Asn Arg Ser Leu Pro Asp
            20                  25                  30

Ile Arg His Pro Asn Cys Asn Ser Lys Arg Tyr Leu Glu Thr Leu Pro
        35                  40                  45

Asn Thr Ser Ile Ile Ile Pro Phe His Asn Glu Gly Trp Ser Ser Leu
    50                  55                  60

Leu Arg Thr Val His Ser Val Leu Asn Arg Ser Pro Pro Glu Leu Val
65                  70                  75                  80

Ala Glu Ile Val Leu Val Asp Asp Phe Ser Asp Arg Glu His Leu Lys
                85                  90                  95

Lys Pro Leu Glu Asp Tyr Met Ala Leu Phe Pro Ser Val Arg Ile Leu
            100                 105                 110

Arg Thr Lys Lys Arg Glu Gly Leu Ile Arg Thr Arg Met Leu Gly Ala
        115                 120                 125
```

```
Ser Val Ala Thr Gly Asp Val Ile Thr Phe Leu Asp Ser His Cys Glu
130                 135                 140
Ala Asn Val Asn Trp Leu Pro Pro Leu Leu Asp Arg Ile Ala Arg Asn
145                 150                 155                 160
Arg Lys Thr Ile Val Cys Pro Met Ile Asp Val Ile Asp His Asp Asp
                165                 170                 175
Phe Arg Tyr Glu Thr Gln Ala Gly Asp Ala Met Arg Gly Ala Phe Asp
            180                 185                 190
Trp Glu Met Tyr Tyr Lys Arg Ile Pro Ile Pro Pro Glu Leu Gln Lys
        195                 200                 205
Ala Asp Pro Ser Asp Pro Phe Glu Ser Pro Val Met Ala Gly Gly Leu
210                 215                 220
Phe Ala Val Asp Arg Lys Trp Phe Trp Glu Leu Gly Gly Tyr Asp Pro
225                 230                 235                 240
Gly Leu Glu Ile Trp Gly Gly Glu Gln Tyr Glu Ile Ser Phe Lys Gly
                245                 250                 255
Leu His Met Leu Pro Arg Leu Val Ser Asn Ser Trp Pro Gln Ala Val
            260                 265                 270
Phe Leu Pro Arg Ala Pro Asn Met Leu Ala Leu Gln Val Trp Met Cys
        275                 280                 285
Gly Gly Arg Met Glu Asp Ile Pro Cys Ser Arg Val Gly His Ile Tyr
290                 295                 300
Arg Lys Tyr Val Pro Tyr Lys Val Pro Ala Gly Val Ser Leu Ala Arg
305                 310                 315                 320
Asn Leu Lys Arg Val Ala Glu Val Trp Met Asp Glu Tyr Ala Glu Tyr
                325                 330                 335
Ile Tyr Gln Arg Arg Pro Glu Tyr Arg His Leu Ser Ala Gly Asp Val
            340                 345                 350
Ala Val Gln Lys Lys Leu Arg Ser Ser Leu Asn Cys Lys Ser Phe Lys
        355                 360                 365
Trp Phe Met Thr Lys Ile Ala Trp Asp Leu Pro Lys Phe Tyr Pro Pro
370                 375                 380
Val Glu Pro Pro Ala Ala Trp Gly Glu Ile Arg Asn Val Gly Thr
385                 390                 395                 400
Gly Leu Cys Ala Asp Thr Lys His Gly Ala Leu Gly Ser Pro Leu Arg
                405                 410                 415
Leu Glu Gly Cys Val Arg Gly Arg Gly Glu Ala Ala Trp Asn Asn Met
            420                 425                 430
Gln Val Phe Thr Phe Thr Trp Arg Glu Asp Ile Arg Pro Gly Asp Pro
        435                 440                 445
Gln His Thr Lys Lys Phe Cys Phe Asp Ala Ile Ser Thr Ser Pro
450                 455                 460
Val Thr Leu Tyr Asp Cys His Ser Met Lys Gly Asn Gln Leu Trp Lys
465                 470                 475                 480
Tyr Arg Lys Asp Lys Thr Leu Tyr His Pro Val Ser Gly Ser Cys Met
                485                 490                 495
Asp Cys Ser Glu Ser Asp His Arg Ile Phe Met Asn Thr Cys Asn Pro
            500                 505                 510
Ser Ser Leu Thr Gln Gln Trp Leu Phe Glu His Thr Asn Ser Thr Val
        515                 520                 525
Leu Glu Lys Phe Asn Arg Asn
530                 535
```

<210> SEQ ID NO 30
<211> LENGTH: 1521
<212> TYPE: DNA
<213> ORGANISM: homo sapiens

<400> SEQUENCE: 30

```
atgaccgatg ctgagagagt ggatcaggca taccgagaaa atggatttaa catctacgtc      60
agtgataaaa tctccttgaa tcgctctctc ccagatatcc ggcacccaaa ctgcaacagc     120
aagcgctacc tggagacact tcccaacaca agcatcatca tcccctttcca caacgagggc    180
tggtcctccc tcctccgcac cgtccacagt gtgctcaatc gctcgcctcc agagctggtc     240
gccgagattg tactggtcga cgacttcagt gatcgagagc acctgaagaa gcctcttgaa     300
gactacatgg ccctttttccc cagtgtgagg attcttcgaa ccaagaaacg ggaagggctg    360
ataaggaccc gaatgctggg ggcctcagtg caactgggg atgtcatcac attcttggat      420
tcacactgtg aagccaatgt caactggctt ccccccttgc ttgaccgcat tgctcggaac     480
cgcaagacca ttgtgtgccc gatgattgat gtaattgacc atgacgactt tcggtacgag     540
acacaggcag gggatgccat gcggggagcc tttgactggg agatgtacta caagcggatc     600
ccgatccctc cagaactgca gaaagctgac cccagcgacc catttgagtc tcccgtgatg     660
gccggtggac tgttcgccgt ggatcggaag tggttctggg aactcggcgg gtatgaccca     720
ggcttggaga tctggggagg ggagcagtat gaaatctcct tcaaggtgtg gatgtgtggg    780
ggccgcatgg aggacatccc ctgctccagg gtgggccata tctacaggaa gtatgtgccc    840
tacaaggtcc cggccggagt cagcctgcc cggaaccttaa gcgggtggc cgaagtgtgg     900
atggatgagt acgcagagta catttaccag cgccggcctg aataccgcca cctctccgct    960
ggggatgtcg cagtccagaa aaagctccgc agctccctta actgcaagag tttcaagtgg  1020
tttatgacga agatagcctg ggacctgccc aaattctacc cacccgtgga gcccccggct  1080
gcagcttggg gggagatccg aaatgtgggc acagggctgt gtgcagacac aaagcacggg  1140
gccttgggct ccccactaag gctagagggc tgcgtccgag gccgtgggga ggctgcctgg  1200
aacaacatgc aggtattcac cttcacctgg agagaggaca tccggcctgg agaccccag   1260
cacaccaaga gttctgcttt tgatgccatt tcccacacca gccctgtcac gctgtacgac  1320
tgccacagca tgaagggcaa ccagctgtgg aaataccgca agacaagac cctgtaccac  1380
cctgtcagtg gcagctgcat ggactgcagt gaaagtgacc ataggatctt catgaacacc  1440
tgcaacccat cctctctcac ccagcagtgg ctgtttgaac acaccaactc aacagtcttg  1500
gaaaaattca ataggaactg a                                             1521
```

<210> SEQ ID NO 31
<211> LENGTH: 506
<212> TYPE: PRT
<213> ORGANISM: homo sapiens

<400> SEQUENCE: 31

```
Met Thr Asp Ala Glu Arg Val Asp Gln Ala Tyr Arg Glu Asn Gly Phe
 1               5                  10                  15

Asn Ile Tyr Val Ser Asp Lys Ile Ser Leu Asn Arg Ser Leu Pro Asp
            20                  25                  30

Ile Arg His Pro Asn Cys Asn Ser Lys Arg Tyr Leu Glu Thr Leu Pro
        35                  40                  45

Asn Thr Ser Ile Ile Ile Pro Phe His Asn Glu Gly Trp Ser Ser Leu
    50                  55                  60
```

```
Leu Arg Thr Val His Ser Val Leu Asn Arg Ser Pro Pro Glu Leu Val
 65                  70                  75                  80

Ala Glu Ile Val Leu Val Asp Asp Phe Ser Asp Arg Glu His Leu Lys
             85                  90                  95

Lys Pro Leu Glu Asp Tyr Met Ala Leu Phe Pro Ser Val Arg Ile Leu
            100                 105                 110

Arg Thr Lys Lys Arg Glu Gly Leu Ile Arg Thr Arg Met Leu Gly Ala
        115                 120                 125

Ser Val Ala Thr Gly Asp Val Ile Thr Phe Leu Asp Ser His Cys Glu
        130                 135                 140

Ala Asn Val Asn Trp Leu Pro Pro Leu Leu Asp Arg Ile Ala Arg Asn
145                 150                 155                 160

Arg Lys Thr Ile Val Cys Pro Met Ile Asp Val Ile Asp His Asp Asp
                165                 170                 175

Phe Arg Tyr Glu Thr Gln Ala Gly Asp Ala Met Arg Gly Ala Phe Asp
                180                 185                 190

Trp Glu Met Tyr Tyr Lys Arg Ile Pro Ile Pro Pro Glu Leu Gln Lys
            195                 200                 205

Ala Asp Pro Ser Asp Pro Phe Glu Ser Pro Val Met Ala Gly Gly Leu
        210                 215                 220

Phe Ala Val Asp Arg Lys Trp Phe Trp Glu Leu Gly Gly Tyr Asp Pro
225                 230                 235                 240

Gly Leu Glu Ile Trp Gly Gly Glu Gln Tyr Glu Ile Ser Phe Lys Val
                245                 250                 255

Trp Met Cys Gly Gly Arg Met Glu Asp Ile Pro Cys Ser Arg Val Gly
                260                 265                 270

His Ile Tyr Arg Lys Tyr Val Pro Tyr Lys Val Pro Ala Gly Val Ser
            275                 280                 285

Leu Ala Arg Asn Leu Lys Arg Val Ala Glu Val Trp Met Asp Glu Tyr
        290                 295                 300

Ala Glu Tyr Ile Tyr Gln Arg Arg Pro Glu Tyr Arg His Leu Ser Ala
305                 310                 315                 320

Gly Asp Val Ala Val Gln Lys Lys Leu Arg Ser Ser Leu Asn Cys Lys
                325                 330                 335

Ser Phe Lys Trp Phe Met Thr Lys Ile Ala Trp Asp Leu Pro Lys Phe
            340                 345                 350

Tyr Pro Pro Val Glu Pro Pro Ala Ala Ala Trp Gly Glu Ile Arg Asn
        355                 360                 365

Val Gly Thr Gly Leu Cys Ala Asp Thr Lys His Gly Ala Leu Gly Ser
        370                 375                 380

Pro Leu Arg Leu Glu Gly Cys Val Arg Gly Arg Gly Glu Ala Ala Trp
385                 390                 395                 400

Asn Asn Met Gln Val Phe Thr Phe Thr Trp Arg Glu Asp Ile Arg Pro
                405                 410                 415

Gly Asp Pro Gln His Thr Lys Lys Phe Cys Phe Asp Ala Ile Ser His
            420                 425                 430

Thr Ser Pro Val Thr Leu Tyr Asp Cys His Ser Met Lys Gly Asn Gln
        435                 440                 445

Leu Trp Lys Tyr Arg Lys Asp Lys Thr Leu Tyr His Pro Val Ser Gly
        450                 455                 460

Ser Cys Met Asp Cys Ser Glu Ser Asp His Arg Ile Phe Met Asn Thr
465                 470                 475                 480

Cys Asn Pro Ser Ser Leu Thr Gln Gln Trp Leu Phe Glu His Thr Asn
```

```
                    485               490                495
Ser Thr Val Leu Glu Lys Phe Asn Arg Asn
                500                505

<210> SEQ ID NO 32
<211> LENGTH: 723
<212> TYPE: DNA
<213> ORGANISM: homo sapiens

<400> SEQUENCE: 32
atgaggcgga aggagaagcg gctcctgcag gcggtggcgc tggtgctggc ggccctggtc    60
ctcctgccca acgtggggct tgggcgctg taccgcgagc ggcagcccga cggcaccct     120
gggggatcgg gggcggcggt ggcgccggcg gcgggacagg gctcacacag tcgacaaaag   180
aaaacgtttt tcttgggaga tgggcagaag ctgaaggact ggcatgacaa ggaggccatc   240
cggagggacg ctcagcgcgt aggaaatgga gaacaaggaa gaccttaccc catgaccgat   300
gctgagagag tggatcaggc ataccgagaa atggattta acatctacgt cagtgataaa   360
atctccttga atcgctctct cccagatatc cggcacccaa actgcaacag caagcgctac   420
ctggagacac ttcccaacac aagcatcatc atcccttcc acaacgaggg ctggtcctcc    480
ctcctccgca ccgtccacag tgtgctcaat cgctcgcctc cagagctggt cgccgagatt   540
gtactggtcg acgacttcag tgatcgaggt aggatccgtc ccacccagcc tcccacctc    600
tgtgcttcat ctggcgactc accaaaggga tggcaggttt ccccttcttt agcagcatca   660
acatataggc atcattggc taaatgcctg gacgttgcac tgtgcacaca ttttctcatt    720
taa                                                                 723

<210> SEQ ID NO 33
<211> LENGTH: 240
<212> TYPE: PRT
<213> ORGANISM: homo sapiens

<400> SEQUENCE: 33

Met Arg Arg Lys Glu Lys Arg Leu Leu Gln Ala Val Ala Leu Val Leu
  1               5                  10                  15

Ala Ala Leu Val Leu Leu Pro Asn Val Gly Leu Trp Ala Leu Tyr Arg
                 20                  25                  30

Glu Arg Gln Pro Asp Gly Thr Pro Gly Gly Ser Gly Ala Ala Val Ala
             35                  40                  45

Pro Ala Ala Gly Gln Gly Ser His Ser Arg Gln Lys Lys Thr Phe Phe
         50                  55                  60

Leu Gly Asp Gly Gln Lys Leu Lys Asp Trp His Asp Lys Glu Ala Ile
 65                  70                  75                  80

Arg Arg Asp Ala Gln Arg Val Gly Asn Gly Glu Gln Gly Arg Pro Tyr
                 85                  90                  95

Pro Met Thr Asp Ala Glu Arg Val Asp Gln Ala Tyr Arg Glu Asn Gly
                100                 105                 110

Phe Asn Ile Tyr Val Ser Asp Lys Ile Ser Leu Asn Arg Ser Leu Pro
            115                 120                 125

Asp Ile Arg His Pro Asn Cys Asn Ser Lys Arg Tyr Leu Glu Thr Leu
        130                 135                 140

Pro Asn Thr Ser Ile Ile Ile Pro Phe His Asn Glu Gly Trp Ser Ser
145                 150                 155                 160

Leu Leu Arg Thr Val His Ser Val Leu Asn Arg Ser Pro Pro Glu Leu
                165                 170                 175
```

```
Val Ala Glu Ile Val Leu Val Asp Asp Phe Ser Asp Arg Gly Arg Ile
            180                 185                 190

Arg Pro Thr Gln Pro Pro Thr Leu Cys Ala Ser Ser Gly Asp Ser Pro
        195                 200                 205

Lys Gly Trp Gln Val Phe Pro Ser Leu Ala Ala Ser Thr Tyr Arg Pro
    210                 215                 220

Ser Leu Ala Lys Cys Leu Asp Val Ala Leu Cys Thr His Phe Leu Ile
225                 230                 235                 240

<210> SEQ ID NO 34
<211> LENGTH: 966
<212> TYPE: DNA
<213> ORGANISM: homo sapiens

<400> SEQUENCE: 34
atgaggcgga aggagaagcg gctcctgcag gcggtggcgc tggtgctggc ggccctggtc      60
ctcctgccca acgtggggct tggggcgctg taccgcgagc ggcagcccga cggcacccct     120
gggggatcgg gggcggcggt ggcgccggcg gcgggacagg gctcacacag tcgacaaaag     180
aaaacgtttt tcttgggaga tgggcagaag ctgaaggact ggcatgacaa ggaggccatc     240
cggagggacg ctcagcgcgt aggaaatgga gaacaaggaa gaccttaccc catgaccgat     300
gctgagagag tggatcaggc ataccgagaa atggattta acatctacgt cagtgataaa      360
atctccttga atcgctctct cccagatatc cggcacccaa actgcaacag caagcgctac     420
ctggagacac ttcccaacac aagcatcatc atcccctccc acaacgaggg ctggtcctcc     480
ctcctccgca ccgtccacag tgtgctcaat cgctcgcctc cagagctggt cgccgagatt     540
gtactggtcg acgacttcag tgatcgagag cacctgaaga agcctcttga agactacatg     600
gcccttttcc ccagtgtgag gattcttcga accaagaaac gggaagggct gataaggacc     660
cgaatgctgg gggcctcagt ggcaactggg gatgtcatca cattcttgga ttcacactgt     720
gaagccaatg tcaactggct tccccccttg cttggtaagg gagcccctcc cacttggagg     780
gaggcaaact gcaatgagcc agtgccagtg gcccctcct gctgcaggga gccatccata    840
agccttccct tgcctgttca agatgccccc agcacaatgc aggtgccat gagggattca     900 gaagttcagg agtgctcaaa attaaaatcc agccagtcct gtcccttcat ttcacagaga     960
agttaa                                                                966

<210> SEQ ID NO 35
<211> LENGTH: 321
<212> TYPE: PRT
<213> ORGANISM: homo sapiens

<400> SEQUENCE: 35

Met Arg Arg Lys Glu Lys Arg Leu Leu Gln Ala Val Ala Leu Val Leu
1               5                   10                  15

Ala Ala Leu Val Leu Leu Pro Asn Val Gly Leu Trp Ala Leu Tyr Arg
            20                  25                  30

Glu Arg Gln Pro Asp Gly Thr Pro Gly Gly Ser Gly Ala Ala Val Ala
        35                  40                  45

Pro Ala Ala Gly Gln Gly Ser His Ser Arg Gln Lys Lys Thr Phe Phe
    50                  55                  60

Leu Gly Asp Gly Gln Lys Leu Lys Asp Trp His Asp Lys Glu Ala Ile
65                  70                  75                  80

Arg Arg Asp Ala Gln Arg Val Gly Asn Gly Glu Gln Gly Arg Pro Tyr
```

```
                     85                  90                  95
Pro Met Thr Asp Ala Glu Arg Val Asp Gln Ala Tyr Arg Glu Asn Gly
                100                 105                 110
Phe Asn Ile Tyr Val Ser Asp Lys Ile Ser Leu Asn Arg Ser Leu Pro
            115                 120                 125
Asp Ile Arg His Pro Asn Cys Asn Ser Lys Arg Tyr Leu Glu Thr Leu
        130                 135                 140
Pro Asn Thr Ser Ile Ile Ile Pro Phe His Asn Glu Gly Trp Ser Ser
145                 150                 155                 160
Leu Leu Arg Thr Val His Ser Val Leu Asn Arg Ser Pro Pro Glu Leu
                165                 170                 175
Val Ala Glu Ile Val Leu Val Asp Asp Phe Ser Asp Arg Glu His Leu
            180                 185                 190
Lys Lys Pro Leu Glu Asp Tyr Met Ala Leu Phe Pro Ser Val Arg Ile
        195                 200                 205
Leu Arg Thr Lys Lys Arg Glu Gly Leu Ile Arg Thr Arg Met Leu Gly
210                 215                 220
Ala Ser Val Ala Thr Gly Asp Val Ile Thr Phe Leu Asp Ser His Cys
225                 230                 235                 240
Glu Ala Asn Val Asn Trp Leu Pro Pro Leu Leu Gly Lys Gly Ala Pro
                245                 250                 255
Pro Thr Trp Arg Glu Ala Asn Cys Asn Glu Pro Val Pro Val Ala Pro
            260                 265                 270
Ser Cys Cys Arg Glu Pro Ser Ile Ser Leu Pro Leu Pro Val Gln Asp
        275                 280                 285
Ala Pro Ser Thr Met Pro Gly Ala Met Arg Asp Ser Glu Val Gln Glu
        290                 295                 300
Cys Ser Lys Leu Lys Ser Ser Gln Ser Cys Pro Phe Ile Ser Gln Arg
305                 310                 315                 320
Ser

<210> SEQ ID NO 36
<211> LENGTH: 630
<212> TYPE: DNA
<213> ORGANISM: homo sapiens

<400> SEQUENCE: 36
atgaggcgga aggagaagcg gctcctgcag gcggtggcgc tggtgctggc ggccctggtc    60
ctcctgccca acgtgggct ttgggcgctg taccgcgagc ggcagcccga cggcacccct   120
gggggatcgg gggcggcggt ggcgccggcg gcgggacagg gctcacacag tcgacaaaag   180
aaaacgtttt tcttgggaga tgggcagaag ctgaaggact ggcatgacaa ggaggccatc   240
cggagggacg ctcagcgcgt aggaaatgga gaacaaggaa gaccttaccc catgaccgat   300
gctgagagag tggatcaggc ataccgagaa aatggattta acatctacgt cagtgataaa   360
atctccttga atcgctctct cccagatatc cggcacccaa actgcaacag caagcgctac   420
ctggagacac ttcccaacac aagcatcatc atccccttcc acaacgaggg ctggtcctcc   480
ctcctccgca ccgtccacag tgtgctcaat cgctcgcctc cagagctggt cgccgagatt   540
gtactggtcg acgacttcag tgatcgagcc atctcttggc ttcttcagac cgcattgctc   600
ggaaccgcaa gaccattgtg tgcccgatga                                     630

<210> SEQ ID NO 37
<211> LENGTH: 209
```

<212> TYPE: PRT
<213> ORGANISM: homo sapiens

<400> SEQUENCE: 37

```
Met Arg Arg Lys Glu Lys Arg Leu Leu Gln Ala Val Ala Leu Val Leu
 1               5                  10                  15
Ala Ala Leu Val Leu Leu Pro Asn Val Gly Leu Trp Ala Leu Tyr Arg
             20                  25                  30
Glu Arg Gln Pro Asp Gly Thr Pro Gly Gly Ser Gly Ala Ala Val Ala
         35                  40                  45
Pro Ala Ala Gly Gln Gly Ser His Ser Arg Gln Lys Lys Thr Phe Phe
     50                  55                  60
Leu Gly Asp Gly Gln Lys Leu Lys Asp Trp His Asp Lys Glu Ala Ile
 65                  70                  75                  80
Arg Arg Asp Ala Gln Arg Val Gly Asn Gly Glu Gln Gly Arg Pro Tyr
                 85                  90                  95
Pro Met Thr Asp Ala Glu Arg Val Asp Gln Ala Tyr Arg Glu Asn Gly
            100                 105                 110
Phe Asn Ile Tyr Val Ser Asp Lys Ile Ser Leu Asn Arg Ser Leu Pro
        115                 120                 125
Asp Ile Arg His Pro Asn Cys Asn Ser Lys Arg Tyr Leu Glu Thr Leu
    130                 135                 140
Pro Asn Thr Ser Ile Ile Ile Pro Phe His Asn Glu Gly Trp Ser Ser
145                 150                 155                 160
Leu Leu Arg Thr Val His Ser Val Leu Asn Arg Ser Pro Pro Glu Leu
                165                 170                 175
Val Ala Glu Ile Val Leu Val Asp Asp Phe Ser Asp Arg Gly Ile Ser
            180                 185                 190
Trp Leu Leu Gln Thr Ala Leu Leu Gly Thr Ala Arg Pro Leu Cys Ala
        195                 200                 205
Arg
```

<210> SEQ ID NO 38
<211> LENGTH: 1101
<212> TYPE: DNA
<213> ORGANISM: homo sapiens

<400> SEQUENCE: 38

```
atgaggcgga aggagaagcg gctcctgcag gcggtggcgc tggtgctggc ggccctggtc    60
ctcctgccca acgtggggct ttgggcgctg taccgcgagc ggcagcccga cggcaccccc   120
gggggatcgg gggcggcggt ggcgccggcg gcgggacagg gctcacacag tcgacaaaag   180
aaaacgtttt tcttgggaga tgggcagaag ctgaaggact ggcatgacaa ggaggccatc   240
cggagggacg ctcagcgcgt aggaaatgga gaacaaggaa gaccttaccc catgaccgat   300
gctgagagag tggatcaggc ataccgagaa atggattta acatctacgt cagtgataaa   360
atctccttga atcgctctct cccagatatc cggcacccaa actgcaacag caagcgctac   420
ctggagacac ttcccaacac aagcatcatc atccccttcc acaacgaggg ctggtcctcc   480
ctcctccgca ccgtccacag tgtgctcaat cgctcgcctc cagagctggt cgccgagatt   540
gtactggtcg acgacttcag tgatcgagag cacctgaaga gcctcttga agactacatg   600
gcccttttcc ccagtgtgag gattcttcga accagaaaac gggaagggct gataaggacc   660
cgaatgctgg gggcctcagt ggcaactggg gatgtcatca cattcttgga ttcacactgt   720
gaagccaatg tcaactggct tcccccttg cttgaccgca ttgctcggaa ccgcaagacc   780
```

```
attgtgtgcc cgatgattga tgtaattgac catgacgact ttcggtacga gacacaggca    840
ggggatgcca tgcggggagc ctttgactgg gagatgtact acaagcggat cccgatccct    900
ccagaactgc agaaagctga ccccagcgac ccatttgagt ctcccgtgat ggccggtgga    960
ctgttcgccg tggatcggaa gtggttctgg gaactcggcg gtatgaccc aggcttggag    1020 atctggggag gggagcagta tgaaatctcc ttcaaggtga gccagctctc agacgcccc    1080 gttcttggca cagcctcctg a                                              1101
```

<210> SEQ ID NO 39
<211> LENGTH: 366
<212> TYPE: PRT
<213> ORGANISM: homo sapiens

<400> SEQUENCE: 39

| | | | | | | | | | | | | | | |
|---|---|---|---|---|---|---|---|---|---|---|---|---|---|---|
| Met | Arg | Arg | Lys | Glu | Lys | Arg | Leu | Leu | Gln | Ala | Val | Ala | Leu | Val | Leu |
| 1 | | | | 5 | | | | | 10 | | | | | 15 | |
| Ala | Ala | Leu | Val | Leu | Leu | Pro | Asn | Val | Gly | Leu | Trp | Ala | Leu | Tyr | Arg |
| | | | 20 | | | | | 25 | | | | | 30 | | |
| Glu | Arg | Gln | Pro | Asp | Gly | Thr | Pro | Gly | Gly | Ser | Gly | Ala | Ala | Val | Ala |
| | | | 35 | | | | | 40 | | | | | 45 | | |
| Pro | Ala | Ala | Gly | Gln | Gly | Ser | His | Ser | Arg | Gln | Lys | Lys | Thr | Phe | Phe |
| | 50 | | | | | 55 | | | | | 60 | | | | |
| Leu | Gly | Asp | Gly | Gln | Lys | Leu | Lys | Asp | Trp | His | Asp | Lys | Glu | Ala | Ile |
| 65 | | | | | 70 | | | | | 75 | | | | | 80 |
| Arg | Arg | Asp | Ala | Gln | Arg | Val | Gly | Asn | Gly | Glu | Gln | Gly | Arg | Pro | Tyr |
| | | | | 85 | | | | | 90 | | | | | 95 | |
| Pro | Met | Thr | Asp | Ala | Glu | Arg | Val | Asp | Gln | Ala | Tyr | Arg | Glu | Asn | Gly |
| | | | 100 | | | | | 105 | | | | | 110 | | |
| Phe | Asn | Ile | Tyr | Val | Ser | Asp | Lys | Ile | Ser | Leu | Asn | Arg | Ser | Leu | Pro |
| | | | 115 | | | | | 120 | | | | | 125 | | |
| Asp | Ile | Arg | His | Pro | Asn | Cys | Asn | Ser | Lys | Arg | Tyr | Leu | Glu | Thr | Leu |
| | 130 | | | | | 135 | | | | | 140 | | | | |
| Pro | Asn | Thr | Ser | Ile | Ile | Ile | Pro | Phe | His | Asn | Glu | Gly | Trp | Ser | Ser |
| 145 | | | | | 150 | | | | | 155 | | | | | 160 |
| Leu | Leu | Arg | Thr | Val | His | Ser | Val | Leu | Asn | Arg | Ser | Pro | Pro | Glu | Leu |
| | | | | 165 | | | | | 170 | | | | | 175 | |
| Val | Ala | Glu | Ile | Val | Leu | Val | Asp | Asp | Phe | Ser | Asp | Arg | Glu | His | Leu |
| | | | 180 | | | | | 185 | | | | | 190 | | |
| Lys | Lys | Pro | Leu | Glu | Asp | Tyr | Met | Ala | Leu | Phe | Pro | Ser | Val | Arg | Ile |
| | | | 195 | | | | | 200 | | | | | 205 | | |
| Leu | Arg | Thr | Lys | Lys | Arg | Glu | Gly | Leu | Ile | Arg | Thr | Arg | Met | Leu | Gly |
| | 210 | | | | | 215 | | | | | 220 | | | | |
| Ala | Ser | Val | Ala | Thr | Gly | Asp | Val | Ile | Thr | Phe | Leu | Asp | Ser | His | Cys |
| 225 | | | | | 230 | | | | | 235 | | | | | 240 |
| Glu | Ala | Asn | Val | Asn | Trp | Leu | Pro | Pro | Leu | Leu | Asp | Arg | Ile | Ala | Arg |
| | | | | 245 | | | | | 250 | | | | | 255 | |
| Asn | Arg | Lys | Thr | Ile | Val | Cys | Pro | Met | Ile | Asp | Val | Ile | Asp | His | Asp |
| | | | 260 | | | | | 265 | | | | | 270 | | |
| Asp | Phe | Arg | Tyr | Glu | Thr | Gln | Ala | Gly | Asp | Ala | Met | Arg | Gly | Ala | Phe |
| | | | 275 | | | | | 280 | | | | | 285 | | |
| Asp | Trp | Glu | Met | Tyr | Tyr | Lys | Arg | Ile | Pro | Ile | Pro | Pro | Glu | Leu | Gln |
| | 290 | | | | | 295 | | | | | 300 | | | | |
| Lys | Ala | Asp | Pro | Ser | Asp | Pro | Phe | Glu | Ser | Pro | Val | Met | Ala | Gly | Gly |

|  |  |  |  |  |
|---|---|---|---|---|
| 305 | 310 | 315 | 320 | |

Leu Phe Ala Val Asp Arg Lys Trp Phe Trp Glu Leu Gly Gly Tyr Asp
                325                 330                 335

Pro Gly Leu Glu Ile Trp Gly Gly Glu Gln Tyr Glu Ile Ser Phe Lys
            340                 345                 350

Val Ser Gln Leu Ser Arg Arg Pro Val Leu Gly Thr Ala Ser
        355                 360                 365

<210> SEQ ID NO 40
<211> LENGTH: 1899
<212> TYPE: DNA
<213> ORGANISM: homo sapiens

<400> SEQUENCE: 40

| | |
|---|---:|
| atgaggcgga aggagaagcg gctcctgcag gcggtggcgc tggtgctggc ggccctggtc | 60 |
| ctcctgccca cgtgggggct ttgggcgctg taccgcgagc ggcagcccga cggcaccccct | 120 |
| gggggatcgg gggcggcggt ggcgccggcg gcgggacagg gctcacacag tcgacaaaag | 180 |
| aaaacgtttt tcttgggaga tgggcagaag ctgaaggact ggcatgacaa ggaggccatc | 240 |
| cggagggacg ctcagcgcgt aggaaatgga gaacaaggaa gaccttaccc catgaccgat | 300 |
| gctgagagag tggatcaggc ataccgagaa aatggattta acatctacgt cagtgataaa | 360 |
| atctccttga atcgctctct cccagatatc cggcacccaa actgcaacag caagcgctac | 420 |
| ctggagacac ttcccaacac aagcatcatc atccccttcc acaacgaggg ctggtcctcc | 480 |
| ctcctccgca ccgtccacag tgtgctcaat cgctcgcctc agagctggtc gccgagatt | 540 |
| gtactggtcg acgacttcag tgatcgagag cacctgaaga agcctcttga agactacatg | 600 |
| gccctttttcc ccagtgtgag gattcttcga accaagaaac gggaagggct gataaggacc | 660 |
| cgaatgctgg gggcctcagt ggcaactggg gatgtcatca cattcttgga ttcacactgt | 720 |
| gaagccaatg tcaactggct tccccccttg cttgaccgca ttgctcggaa ccgcaagacc | 780 |
| attgtgtgcc cgatgattga tgtaattgac catgacgact ttcggtacga gacacaggca | 840 |
| ggggatgcca tgcgggagcc ctttgactgg gagatgtact acaagcggat cccgatccct | 900 |
| ccagaactgc agaaagctga ccccagcgac ccatttgagt ctcccgtgat ggccggtgga | 960 |
| ctgttcgccg tggatcggaa gtggttctgg gaactcggcg gtatgaccc aggcttggag | 1020 |
| atctggggag gggagcagta tgaaatctcc ttcaagggtc tccatatgtt gcccaggctg | 1080 |
| gtctcaaact cctggcctca agcagtcttc ctgcctcggg ctcccaacat gctggcatta | 1140 |
| caggtgtgga tgtgtggggg ccgcatggag gacatcccct gctccagggt gggccatatc | 1200 |
| tacaggaagt atgtgcccta caaggtcccg gccggagtca gcctggcccg gaaccttaag | 1260 |
| cgggtggccg aagtgtggat ggatgagtac gcagagtaca tttaccagcg ccggcctgaa | 1320 |
| taccgccacc tctccgctgg ggatgtcgca gtccagaaaa agctccgcag ctcccttaac | 1380 |
| tgcaagagtt tcaagtggtt tatgacgaag atagcctggg acctgccaa attctaccca | 1440 |
| cccgtggagc ccccggctgc agcttggggg gagatccgaa atgtgggcac agggctgtgt | 1500 |
| gcagacacaa agcacggggc cttgggctcc ccactaaggc tagagggctg cgtccgaggc | 1560 |
| cgtgggggagg ctgcctggaa caacatgcag gtattcacct tcacctggag agaggacatc | 1620 |
| cggcctggag accccagca caccaagaag ttctgctttg atgccatttc ccacaccagc | 1680 |
| cctgtcacgc tgtacgactg ccacagcatg aagggcaacc agctgtggaa ataccgcaaa | 1740 |
| gacaagaccc tgtaccaccc tgtcagtggc agctgcatgg actgcagtga aagtgaccat | 1800 |

-continued

```
aggatcttca tgaacacctg caacccatcc tctctcaccc agcagtggct gtttgaacac    1860
accaactcaa cagtcttgga aaaattcaat aggaactga                           1899
```

<210> SEQ ID NO 41
<211> LENGTH: 631
<212> TYPE: PRT
<213> ORGANISM: homo sapiens

<400> SEQUENCE: 41

```
Met Arg Arg Lys Glu Lys Arg Leu Leu Gln Ala Val Ala Leu Val Leu
  1               5                  10                  15

Ala Ala Leu Val Leu Leu Pro Asn Val Gly Leu Trp Ala Leu Tyr Arg
                 20                  25                  30

Glu Arg Gln Pro Asp Gly Thr Pro Gly Gly Ser Gly Ala Ala Val Ala
             35                  40                  45

Pro Ala Ala Gly Gln Gly Ser His Ser Arg Gln Lys Lys Thr Phe Phe
         50                  55                  60

Leu Gly Asp Gly Gln Lys Leu Lys Asp Trp His Asp Lys Glu Ala Ile
 65                  70                  75                  80

Arg Arg Asp Ala Gln Arg Val Gly Asn Gly Glu Gln Gly Arg Pro Tyr
                 85                  90                  95

Pro Met Thr Asp Ala Glu Arg Val Asp Gln Ala Tyr Arg Glu Asn Gly
                100                 105                 110

Phe Asn Ile Tyr Val Ser Asp Lys Ile Ser Leu Asn Arg Ser Leu Pro
            115                 120                 125

Asp Ile Arg His Pro Asn Cys Asn Ser Lys Arg Tyr Leu Glu Thr Leu
        130                 135                 140

Pro Asn Thr Ser Ile Ile Ile Pro Phe His Asn Glu Gly Trp Ser Ser
145                 150                 155                 160

Leu Leu Arg Thr Val His Ser Val Leu Asn Arg Ser Pro Pro Glu Leu
                165                 170                 175

Val Ala Glu Ile Val Leu Val Asp Asp Phe Ser Asp Arg Glu His Leu
            180                 185                 190

Lys Lys Pro Leu Glu Asp Tyr Met Ala Leu Phe Pro Ser Val Arg Ile
        195                 200                 205

Leu Arg Thr Lys Lys Arg Glu Gly Leu Ile Arg Thr Arg Met Leu Gly
    210                 215                 220

Ala Ser Val Ala Thr Gly Asp Val Ile Thr Phe Leu Asp Ser His Cys
225                 230                 235                 240

Glu Ala Asn Val Asn Trp Leu Pro Leu Leu Asp Arg Ile Ala Arg
                245                 250                 255

Asn Arg Lys Thr Ile Val Cys Pro Met Ile Asp Val Ile Asp His Asp
            260                 265                 270

Asp Phe Arg Tyr Glu Thr Gln Ala Gly Asp Ala Met Arg Gly Ala Phe
        275                 280                 285

Asp Trp Glu Met Tyr Tyr Lys Arg Ile Pro Ile Pro Pro Glu Leu Gln
    290                 295                 300

Lys Ala Asp Pro Ser Asp Pro Phe Glu Ser Pro Val Met Ala Gly Gly
305                 310                 315                 320

Leu Phe Ala Val Asp Arg Lys Trp Phe Trp Glu Leu Gly Gly Tyr Asp
                325                 330                 335

Pro Gly Leu Glu Ile Trp Gly Gly Glu Gln Tyr Glu Ile Ser Phe Lys
            340                 345                 350

Gly Leu His Met Leu Pro Arg Leu Val Ser Asn Ser Trp Pro Gln Ala
```

```
                355                 360                 365
Val Phe Leu Pro Arg Ala Pro Asn Met Leu Ala Leu Gln Val Trp Met
    370                 375                 380

Cys Gly Gly Arg Met Glu Asp Ile Pro Cys Ser Arg Val Gly His Ile
385                 390                 395                 400

Tyr Arg Lys Tyr Val Pro Tyr Lys Val Pro Ala Gly Val Ser Leu Ala
                405                 410                 415

Arg Asn Leu Lys Arg Val Ala Glu Val Trp Met Asp Glu Tyr Ala Glu
            420                 425                 430

Tyr Ile Tyr Gln Arg Arg Pro Glu Tyr Arg His Leu Ser Ala Gly Asp
        435                 440                 445

Val Ala Val Gln Lys Lys Leu Arg Ser Ser Leu Asn Cys Lys Ser Phe
    450                 455                 460

Lys Trp Phe Met Thr Lys Ile Ala Trp Asp Leu Pro Lys Phe Tyr Pro
465                 470                 475                 480

Pro Val Glu Pro Pro Ala Ala Ala Trp Gly Glu Ile Arg Asn Val Gly
                485                 490                 495

Thr Gly Leu Cys Ala Asp Thr Lys His Gly Ala Leu Gly Ser Pro Leu
            500                 505                 510

Arg Leu Glu Gly Cys Val Arg Gly Arg Gly Glu Ala Ala Trp Asn Asn
        515                 520                 525

Met Gln Val Phe Thr Phe Thr Trp Arg Glu Asp Ile Arg Pro Gly Asp
    530                 535                 540

Pro Gln His Thr Lys Lys Phe Cys Phe Asp Ala Ile Ser His Thr Ser
545                 550                 555                 560

Pro Val Thr Leu Tyr Asp Cys His Ser Met Lys Gly Asn Gln Leu Trp
                565                 570                 575

Lys Tyr Arg Lys Asp Lys Thr Leu Tyr His Pro Val Ser Gly Ser Cys
            580                 585                 590

Met Asp Cys Ser Glu Ser Asp His Arg Ile Phe Met Asn Thr Cys Asn
        595                 600                 605

Pro Ser Ser Leu Thr Gln Gln Trp Leu Phe Glu His Thr Asn Ser Thr
    610                 615                 620

Val Leu Glu Lys Phe Asn Asn
625                 630

<210> SEQ ID NO 42
<211> LENGTH: 1812
<212> TYPE: DNA
<213> ORGANISM: homo sapiens

<400> SEQUENCE: 42
atgaggcgga aggagaagcg gctcctgcag gcggtggcgc tggtgctggc ggccctggtc      60
ctcctgccca acgtggggct ttgggcgctg taccgcgagc ggcagcccga cggcacccct     120
gggggatcgg gggcggcggt ggcgccggcg gcgggacagg gctcacacag tcgacaaaag     180
aaaacgtttt tcttgggaga tgggcagaag ctgaaggact ggcatgacaa ggaggccatc     240
cggagggacg ctcagcgcgt aggaaatgga gaacaaggaa gaccttaccc catgaccgat     300
gctgagagag tggatcaggc ataccgagaa aatggattta acatctacgt cagtgataaa     360
atctccttga atcgctctct cccagatatc cggcacccaa actgcaacag caagcgctac     420
ctggagacac ttcccaacac aagcatcatc atccccttcc acaacgaggg ctggtcctcc     480
ctcctccgca ccgtccacag tgtgctcaat cgctcgcctc cagagctggt cgccgagatt     540
```

-continued

```
gtactggtcg acgacttcag tgatcgagag cacctgaaga agcctcttga agactacatg   600
gcccttttcc ccagtgtgag gattcttcga accaagaaac gggaagggct gataaggacc   660
cgaatgctgg gggcctcagt ggcaactggg gatgtcatca cattcttgga ttcacactgt   720
gaagccaatg tcaactggct tccccccttg cttgaccgca ttgctcggaa ccgcaagacc   780
attgtgtgcc cgatgattga tgtaattgac catgacgact ttcggtacga gacacaggca   840
ggggatgcca tgcggggagc cttttgactgg gagatgtact acaagcggat cccgatccct   900
ccagaactgc agaaagctga ccccagcgac ccatttgagt ctcccgtgat ggccggtgga   960
ctgttcgccg tggatcggaa gtggttctgg gaactcggcg gtatgaccc aggcttggag   1020
atctggggag gggagcagta tgaaatctcc ttcaaggtgt ggatgtgtgg gggccgcatg   1080
gaggacatcc cctgctccag ggtgggccat atctacagga agtatgtgcc ctacaaggtc   1140
ccggccggag tcagcctggc ccggaacctt aagcgggtgg ccgaagtgtg gatggatgag   1200
tacgcagagt acatttacca cgccggcct gaataccgcc acctctccgc tggggatgtc   1260
gcagtccaga aaaagctccg cagctccctt aactgcaaga gtttcaagtg gtttatgacg   1320
aagatagcct gggacctgcc caaattctac ccacccgtgg agccccggc tgcagcttgg   1380
ggggagatcc gaaatgtggg cacagggctg tgtgcagaca caaagcacgg ggccttgggc   1440
tccccactaa ggctagaggg ctgcgtccga ggccgtgggg aggctgcctg gaacaacatg   1500
caggtattca ccttcacctg gagagaggac atccggcctg gagaccccca gcacaccaag   1560
aagttctgct ttgatgccat tcccacacc agccctgtca cgctgtacga ctgccacagc   1620
atgaagggca accagctgtg gaaataccgc aaagacaaga ccctgtacca ccctgtcagt   1680
ggcagctgca tggactgcag tgaaagtgac cataggatct tcatgaacac ctgcaaccca   1740
tcctctctca cccagcagtg gctgtttgaa cacaccaact caacagtctt ggaaaaattc   1800
aataggaact ga                                                      1812
```

<210> SEQ ID NO 43
<211> LENGTH: 603
<212> TYPE: PRT
<213> ORGANISM: homo sapiens

<400> SEQUENCE: 43

```
Met Arg Arg Lys Glu Lys Arg Leu Leu Gln Ala Val Ala Leu Val Leu
  1               5                  10                  15

Ala Ala Leu Val Leu Leu Pro Asn Val Gly Leu Trp Ala Leu Tyr Arg
                 20                  25                  30

Glu Arg Gln Pro Asp Gly Thr Pro Gly Gly Ser Gly Ala Ala Val Ala
             35                  40                  45

Pro Ala Ala Gly Gln Gly Ser His Ser Arg Gln Lys Lys Thr Phe Phe
         50                  55                  60

Leu Gly Asp Gly Gln Lys Leu Lys Asp Trp His Asp Lys Glu Ala Ile
 65                  70                  75                  80

Arg Arg Asp Ala Gln Arg Val Gly Asn Gly Glu Gln Gly Arg Pro Tyr
                 85                  90                  95

Pro Met Thr Asp Ala Glu Arg Val Asp Gln Ala Tyr Arg Glu Asn Gly
                100                 105                 110

Phe Asn Ile Tyr Val Ser Asp Lys Ile Ser Leu Asn Arg Ser Leu Pro
            115                 120                 125

Asp Ile Arg His Pro Asn Cys Asn Ser Lys Arg Tyr Leu Glu Thr Leu
        130                 135                 140
```

-continued

```
Pro Asn Thr Ser Ile Ile Pro Phe His Asn Glu Gly Trp Ser Ser
145                 150                 155                 160

Leu Leu Arg Thr Val His Ser Val Leu Asn Arg Ser Pro Pro Glu Leu
            165                 170                 175

Val Ala Glu Ile Val Leu Val Asp Asp Phe Ser Asp Arg Glu His Leu
            180                 185                 190

Lys Lys Pro Leu Glu Asp Tyr Met Ala Leu Phe Pro Ser Val Arg Ile
            195                 200                 205

Leu Arg Thr Lys Lys Arg Glu Gly Leu Ile Arg Thr Arg Met Leu Gly
            210                 215                 220

Ala Ser Val Ala Thr Gly Asp Val Ile Thr Phe Leu Asp Ser His Cys
225                 230                 235                 240

Glu Ala Asn Val Asn Trp Leu Pro Pro Leu Leu Asp Arg Ile Ala Arg
            245                 250                 255

Asn Arg Lys Thr Ile Val Cys Pro Met Ile Asp Val Ile Asp His Asp
            260                 265                 270

Asp Phe Arg Tyr Glu Thr Gln Ala Gly Asp Ala Met Arg Gly Ala Phe
            275                 280                 285

Asp Trp Glu Met Tyr Tyr Lys Arg Ile Pro Ile Pro Pro Glu Leu Gln
            290                 295                 300

Lys Ala Asp Pro Ser Asp Pro Phe Glu Ser Pro Val Met Ala Gly Gly
305                 310                 315                 320

Leu Phe Ala Val Asp Arg Lys Trp Phe Trp Glu Leu Gly Gly Tyr Asp
            325                 330                 335

Pro Gly Leu Glu Ile Trp Gly Gly Glu Gln Tyr Glu Ile Ser Phe Lys
            340                 345                 350

Val Trp Met Cys Gly Gly Arg Met Glu Asp Ile Pro Cys Ser Arg Val
            355                 360                 365

Gly His Ile Tyr Arg Lys Tyr Val Pro Tyr Lys Val Pro Ala Gly Val
            370                 375                 380

Ser Leu Ala Arg Asn Leu Lys Arg Val Ala Glu Val Trp Met Asp Glu
385                 390                 395                 400

Tyr Ala Glu Tyr Ile Tyr Gln Arg Arg Pro Glu Tyr Arg His Leu Ser
            405                 410                 415

Ala Gly Asp Val Ala Val Gln Lys Lys Leu Arg Ser Ser Leu Asn Cys
            420                 425                 430

Lys Ser Phe Lys Trp Phe Met Thr Lys Ile Ala Trp Asp Leu Pro Lys
            435                 440                 445

Phe Tyr Pro Pro Val Glu Pro Pro Ala Ala Ala Trp Gly Glu Ile Arg
            450                 455                 460

Asn Val Gly Thr Gly Leu Cys Ala Asp Thr Lys His Gly Ala Leu Gly
465                 470                 475                 480

Ser Pro Leu Arg Leu Glu Gly Cys Val Arg Gly Arg Gly Glu Ala Ala
            485                 490                 495

Trp Asn Asn Met Gln Val Phe Thr Phe Thr Trp Arg Glu Asp Ile Arg
            500                 505                 510

Pro Gly Asp Pro Gln His Thr Lys Phe Cys Phe Asp Ala Ile Ser
            515                 520                 525

His Thr Ser Pro Val Thr Leu Tyr Asp Cys His Ser Met Lys Gly Asn
            530                 535                 540

Gln Leu Trp Lys Tyr Arg Lys Asp Lys Thr Leu Tyr His Pro Val Ser
545                 550                 555                 560

Gly Ser Cys Met Asp Cys Ser Glu Ser Asp His Arg Ile Phe Met Asn
```

|     |     |     |     |     |
| --- | --- | --- | --- | --- |
| 565 | | 570 | | 575 |
| Thr Cys Asn Pro Ser | Ser Leu Thr Gln Gln | Trp Leu Phe Glu His Thr | | |
| | 580 | | 585 | 590 |
| Asn Ser Thr Val Leu | Glu Lys Phe Asn Arg Asn | | | |
| | 595 | 600 | | |

<210> SEQ ID NO 44
<211> LENGTH: 3896
<212> TYPE: DNA
<213> ORGANISM: homo sapiens

<400> SEQUENCE: 44

| | |
|---|---|
| ccggccccga tgaggcggaa ggagaagcgg ctcctgcagg cggtggcgct ggtgctggcg | 60 |
| gccctggtcc tcctgcccaa cgtgggctt tgggcgctgt accgcgagcg gcagcccgac | 120 |
| ggcacccctg ggggatcggg ggcggcggtg gcgccggcgg cgggacaggg ctcacacagt | 180 |
| cgacaaaaga aaacgttttt cttgggagat gggcagaagc tgaaggactg gcatgacaag | 240 |
| gaggccatcc ggagggacgc tcagcgcgta ggaaatggag aacaaggaag accttacccc | 300 |
| atgaccgatg ctgagagagt ggatcaggca taccgagaaa atggatttaa catctacgtc | 360 |
| agtgataaaa tctccttgaa tcgctctctc ccagatatcc ggcacccaaa ctgcaacagc | 420 |
| aagcgctacc tggagacact tcccaacaca agcatcatca tccccttcca caacgagggc | 480 |
| tggtcctccc tcctccgcac cgtccacagt gtgctcaatc gctcgcctcc agagctggtc | 540 |
| gccgagattt actggtcga cgacttcagt gatcgagagc acctgaagaa gcctcttgaa | 600 |
| gactacatgg cccttttccc cagtgtgagg attcttcgaa ccaagaaacg ggaagggctg | 660 |
| ataaggaccc gaatgctggg ggcctcagtg caactgggg atgtcatcac attcttggat | 720 |
| tcacactgtg aagccaatgt caactggctt cccccttgc ttgaccgcat tgctcggaac | 780 |
| cgcaagacca ttgtgtgccc gatgattgat gtaattgacc atgacgactt tcggtacgag | 840 |
| acacaggcag gggatgccat gcggggagcc tttgactggg agatgtacta caagcggatc | 900 |
| ccgatccctc cagaactgca gaaagctgac cccagcgacc catttgagtc tccccgtgatg | 960 |
| gccggtggac tgttcgccgt ggatcggaag tggttctggg aactcggcgg gtatgaccca | 1020 |
| ggcttggaga tctggggagg ggagcagtat gaaatctcct tcaaggtgtg gatgtgtggg | 1080 |
| ggccgcatgg aggacatccc ctgctccagg gtgggccata tctacaggaa gtatgtgccc | 1140 |
| tacaaggtcc cggccggagt cagcctggcc cggaaccta gcgggtggc cgaagtgtgg | 1200 |
| atggatgagt acgcagagta catttaccag cgccggcctg aataccgcca cctctccgct | 1260 |
| ggggatgtcg cagtccagaa aaagctccgc agctccctta actgcaagag tttcaagtgg | 1320 |
| tttatgacga agatagcctg ggacctgccc aaattctacc cacccgtgga gccccggct | 1380 |
| gcagcttggg gggagatccg aaatgtgggc acagggctgt gtgcagacac aaagcacggg | 1440 |
| gccttgggct ccccactaag gctagagggc tgcgtccgag gccgtgggga ggctgcctgg | 1500 |
| aacaacatgc aggtattcac cttcacctgg agagaggaca tccggcctgg agacccccag | 1560 |
| cacaccaaga agttctgctt tgatgccatt tcccacacca gccctgtcac gctgtacgac | 1620 |
| tgccacagca tgaagggcaa ccagctgtgg aaataccgca agacaagac cctgtaccac | 1680 |
| cctgtcagtg gcagctgcat ggactgcagt gaaagtgacc ataggatctt catgaacacc | 1740 |
| tgcaacccat cctctctcac ccagcagtgg ctgtttgaac acaccaactc aacagtcttg | 1800 |
| gaaaaattca ataggaactg agccctcatg tccccttggc aggcccccca gggtctggca | 1860 |
| ctcactgcag acttcctctt tcaagggagg cagggcccct gtgggcacta ggtgtaaaag | 1920 |

-continued

```
gtgctggcca atggttcag ggtgaagagg gctcttgatt caggggctgg ggtctgcctg      1980
gtccttgagc ccctgagttg tggggtagg gtgaagagca tatcccacag aggccccaca      2040
gggagcagag actgctttaa tccctgctga catcacggaa aagcaacaga gccttttcaa      2100 cttttgtcact atgtccccctt gaacattatg tgggagaaca ccaaggtagc ctaggccacc    2160
caaaagtgag tcctgcgagg ttgcccagcc ctcagatggc tctcctacat gatggtgctt      2220
tagaaacaaa ggtaaaattt gcctgtttgg ggcagctttt agtatcgatg ccactcatct      2280
gcagcagaag agaaagaagt cctcttgggg ctttttagtt tctgccgtcc tgggggaac       2340 attgcagtta ctgcacagct tctgttctct gtcacaaccc caggtgattt ggtccggtca      2400
aaggccatac ttgggcccct aagagtgttc agtattgaat gctgatcagc tgccaggtga      2460
ggagtcagaa gagggagccc ccctagacat ttctttgcag ctatggacat gcgggatatc      2520 tcccctgct ctctgggtat ttgaaatgtc aattttagca ctctccaggc acaaggacag       2580
cccagcacca gctttacagg gcagtgtttc agatggccct gagcccacgg aaaaggccag      2640
gtagacctcc aaactagaaa tgctggctga tttgccctga tccatgcttc catttccctg      2700
tctctcttcc ccaggcaatt actggcctca aaagaggaac agaggtgctg cgaggtgctc       2760
acctcacaga gtctggaggc ctccaggatc aactgtgggc aaagtgcctg cctctgacct      2820
catcatggtt ctagttctca tacagaactc cagaattttt aaagaactct ataattggat      2880
tgcaaactag gatgctacat aggattctgg tattccacat ccaatatgga tttctagaat      2940
gctgtgatta aaggagccag ccaggtgtaa tacagtcaag gcagccccca gcctagagac      3000
aatctgtgaa atccaaagtt ggtggtgttg ggaaagcagg gggacatgtg tccctcagct      3060
cagcagaggc tgtggtacaa catggtcctt ggtgaagacc tgcaccctg gaacctccca       3120 ccatcatcac aactgtagtc tcatttgcag tggagaaaag aacccgacgt cccacagcca      3180
gatatacacc cagctccatg ccagcccttc atgtttacct tttgctttgt taattacatg      3240
tcagactcct agagggcctc cagactaata ggaagcattt ctgtaaccaa cctgccaccc      3300
actgattcag aaatgaaat cacattccac aatctatggc ttccaccagc tagcccagga       3360
aatacttgaa atcagcattc caattagtgt tgagtctctt gattgtgtca tttaccaatt      3420
aaataactga gacctaagtc tgggaacaga gccacgaatc tgcctttgag atgctggcag      3480
atctcaaggc catcaattat tggggaggg aggacaaac actcccaatc atccaccagt       3540
cagactgaat gtgtagctgg cgaggaatta cttccacttc tggcccagca caagccctgc      3600
tttggccacc tgtctgcaag agaggcggcc cctgtgcttg caacgcttac gtgttgatcc      3660
cagtgtcctt ttccaaatga gtgctgtagc tttagaagtg gccctctata gaaagaagtc      3720
aaaagatgag gccccttcta gaatctagga taacaagagt gttgacagtt tgaggagtcg      3780
aattgagatt catcatcaaa gagcaatgca gcgtcgttaa aataaaaact gtgccttta       3840 aaagaaaaa tgcaaatata gagcaaatcc ctaaacttga aaaaaaaaa aaaaaa            3896
```

<210> SEQ ID NO 45
<211> LENGTH: 555
<212> TYPE: DNA
<213> ORGANISM: homo sapiens

<400> SEQUENCE: 45

```
atgaaacctg atgaaactcc tatgtttgac ccaagtctac tcaaagaagt ggactggagt       60
cagaatacag ctacattttc tccagccatt tccccaacac atcctggaga aggcttggtt      120
```

```
ttgaggcctc tttgtactgc tgacttaaat agaggttttt ttaaggtatt gggtcagcta      180
acagagactg gagttgtcag ccctgaacaa tttatgaaat cttttgagca tatgaagaaa      240
tctggggatt attatgttac agttgtagaa gatgtgactc taggacagat tgttgctacg      300
gcaactctga ttatagaaca taaattcatc cattcctgtg ctaagagagg aagagtagaa      360
gatgttgttg ttagtgatga atgcagagga aagcagcttg gcaaattgtt attatcaacc      420
cttactttgc taagcaagaa actgaactgt acaagatta cccttgaatg tctaccacaa      480
aatgttggtt tctataaaaa ggttggatat actgtatctg aagaaaacta catgtgtcgg      540
aggtttctaa agtaa                                                     555

<210> SEQ ID NO 46
<211> LENGTH: 184
<212> TYPE: PRT
<213> ORGANISM: homo sapiens

<400> SEQUENCE: 46

Met Lys Pro Asp Glu Thr Pro Met Phe Asp Pro Ser Leu Leu Lys Glu
  1               5                  10                  15

Val Asp Trp Ser Gln Asn Thr Ala Thr Phe Ser Pro Ala Ile Ser Pro
             20                  25                  30

Thr His Pro Gly Glu Gly Leu Val Leu Arg Pro Leu Cys Thr Ala Asp
         35                  40                  45

Leu Asn Arg Gly Phe Phe Lys Val Leu Gly Gln Leu Thr Glu Thr Gly
     50                  55                  60

Val Val Ser Pro Glu Gln Phe Met Lys Ser Phe Glu His Met Lys Lys
 65                  70                  75                  80

Ser Gly Asp Tyr Tyr Val Thr Val Glu Asp Val Thr Leu Gly Gln
                 85                  90                  95

Ile Val Ala Thr Ala Thr Leu Ile Ile Glu His Lys Phe Ile His Ser
                100                 105                 110

Cys Ala Lys Arg Gly Arg Val Glu Asp Val Val Ser Asp Glu Cys
            115                 120                 125

Arg Gly Lys Gln Leu Gly Lys Leu Leu Leu Ser Thr Leu Thr Leu Leu
        130                 135                 140

Ser Lys Lys Leu Asn Cys Tyr Lys Ile Thr Leu Glu Cys Leu Pro Gln
145                 150                 155                 160

Asn Val Gly Phe Tyr Lys Lys Val Gly Tyr Thr Val Ser Glu Glu Asn
                165                 170                 175

Tyr Met Cys Arg Arg Phe Leu Lys
            180

<210> SEQ ID NO 47
<211> LENGTH: 795
<212> TYPE: DNA
<213> ORGANISM: homo sapiens

<400> SEQUENCE: 47
cctccgctcg cctgcgcgcg gccctgcgtg aggggcaga ggcgaggtgg aggcgttggc       60
gctgccacgt ctgggccgcg gttcccaact gtggcgcggg cggtggagga ggaggtgggg     120
ctggcgctga agccggatcc ggatccggtc tgtgcacac tggtggggga gagtccgacg     180
cgcctggcta ggagcgccga ccgcaggggc ctctacggac cttactagaa aaatgaaacc     240
tgatgaaact cctatgtttg acccaagtct actcaaagaa gtggactgga gtcagaatac     300
agctacattt tctccagcca tttccccaac acatcctgga gaaggcttgg ttttgaggcc     360
```

```
tctttgtact gctgacttaa atagaggttt ttttaaggta ttgggtcagc taacagagac    420
tggagttgtc agccctgaac aatttatgaa atcttttgag catatgaaga aatctgggga    480
ttattatgtt acagttgtag aagatgtgac tctaggacag attgttgcta cggcaactct    540
gattatagaa cataaattca tccattcctg tgctaagaga ggaagagtag aagatgttgt    600
tgttagtgat gaatgcagag gaaagcagct tggcaaattg ttattatcaa cccttacttt    660
gctaagcaag aaactgaact gttacaagat tacccttgaa tgtctaccac aaaatgttgg    720
tttctataaa aaggttggat atactgtatc tgaagaaaac tacatgtgtc ggaggtttct    780
aaagtaaaaa tcttg                                                     795
```

HUMAN TRANSFERASE PROTEINS AND POLYNUCLEOTIDES ENCODING THE SAME

The present application is a divisional of U.S. application Ser. No. 09/795,926, filed Feb. 28, 2001, now U.S. Pat. No. 6,555,669 which claims the benefit of U.S. Provisional Application No. 60/185,920, which was filed on Feb. 29, 2000, U.S. Provisional Application No. 60/186,558, which was filed on Mar. 2, 2000, and U.S. Provisional Application No. 60/191,849, which was filed on Mar. 24, 2000, each of which are herein incorporated by reference in their entirety.

1. INTRODUCTION

The present invention relates to the discovery, identification, and characterization of novel human polynucleotides encoding proteins that share sequence similarity with mammalian transferase proteins such as, but not limited to, sulfotransferases and N-acetyl-galactosaminyltransferases. The invention encompasses the described polynucleotides, host cell expression systems, the encoded proteins, fusion proteins, polypeptides and peptides, antibodies to the encoded proteins and peptides, and genetically engineered animals that either lack or over express the disclosed polynucleotides, antagonists and agonists of the proteins, and other compounds that modulate the expression or activity of the proteins encoded by the disclosed polynucleotides that can be used for diagnosis, drug screening, clinical trial monitoring, and treatment of diseases and disorders.

2. BACKGROUND OF THE INVENTION

Transferases are biologically active proteins that covalently modify molecules such as biological substrates, including proteins, as part of degradation, maturation, and secretory pathways within the body. Transferases have thus been associated with, inter alia, development, immunity, cell replication, gene expression, cancer, protein and cellular senescence, hyperproliferative disorders and as cancer associated markers. In particular, transferases have been implicated in, inter alia, immune function and Parkinson's Disease.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with mammalian sulfotransferases, N-acetyl-galactosaminyltransferases and transferase proteins.

The novel human nucleic acid (cDNA) sequences described herein encode proteins/open reading frames (ORFs) of 303, 110, 265, 148, 148, 186, 59, 214, and 97 amino acids in length (sulfotransferases, SEQ ID NOS: 2, 4, 6, 8, 10, 12, 14, 16, and 18); 143, 224, 112, 269, 535, 506, 240, 321, 209, 366, 631, and 603 amino acids in length (N-acetyl-galactosaminyltransferases, SEQ ID NOS: 21, 23, 25, 27, 29, 31, 33, 35, 37, 39, 41, and 43 respectively); and 184 amino acids in length (transferases, SEQ ID NO:46).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP polynucleotides (e.g., expression constructs that place the described polynucleotide under the control of a strong promoter system), and transgenic animals that express a NHP transgene, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–47 are "knocked-out" they provide a method of identifying phenotypic expression of the particular gene as well as a method of assigning function to previously unknown genes. Additionally, the unique NHP sequences described in SEQ ID NOS:1–47 are useful for the identification of coding sequence and the mapping a unique gene to a particular chromosome.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the described NHP ORFs that encode the described NHP amino acid sequences. SEQ ID NOS: 19, 44, and 47 describe nucleotides encoding NHP ORFs along with regions of flanking sequence.

5. DETAILED DESCRIPTION OF THE INVENTION

The NHPs described for the first time herein are novel proteins that may be expressed in, inter alia, human cell lines, human fetal brain, brain, pituitary, cerebellum, spinal cord, thymus, spleen, lymph node, bone marrow, trachea, kidney, fetal liver, liver, prostate, testis, thyroid, adrenal gland, pancreas, salivary gland, stomach, small intestine, colon, skeletal muscle, heart, uterus, placenta, mammary gland, adipose, esophagus, bladder, cervix, rectum, pericardium, hypothalamus, ovary, fetal kidney, fetal lung, and gene trapped cells.

More particularly, the NHP that are similar to sulfotransferases is predominantly found in testis. The N-acetyl-galactosaminyltransferase-like NHP can be found expressed in the human fetal brain, brain, pituitary, cerebellum, spinal cord, thymus, spleen, lymph node, bone marrow, trachea, kidney, fetal liver, liver, prostate, testis, thyroid, adrenal gland, pancreas, salivary gland, stomach, small intestine, colon, uterus, placenta, mammary gland, adipose, esophagus, bladder, cervix, rectum, pericardium, hypothalamus, ovary and fetal lung. The NHP that is similar to transferase protein is expressed in human fetal brain, brain, pituitary, cerebellum, spinal cord, thymus, spleen, lymph node, bone marrow, trachea, kidney, fetal liver, liver, prostate, testis, thyroid, adrenal gland, pancreas, salivary gland, stomach, small intestine, colon, skeletal muscle, uterus, mammary gland, adipose, skin, esophagus, cervix, rectum, pericardium, hypothalamus, ovary, fetal kidney and fetal lung.

The present invention encompasses the nucleotides presented in the Sequence Listing, host cells expressing such nucleotides, the expression products of such nucleotides, and: (a) nucleotides that encode mammalian homologs of the described polynucleotides, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal (or hydrophobic transmembrane) sequence is deleted; (d) nucleotides that encode chimeric fusion proteins containing all or a portion of a coding region of an NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the, described NHP sequences. An oligonucleotide or polynucleotide sequence first disclosed in at least a portion of one or more of the sequences of SEQ ID NOS: 1–47 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–47, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–47 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–47.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms.

The use of addressable arrays comprising sequences first disclosed in SEQ ID NOS:1–47 provides detailed information about transcriptional changes involved in a specific pathway, potentially leading to the identification of novel components or gene functions that manifest themselves as novel phenotypes.

Probes consisting of sequences first disclosed in SEQ ID NOS:1–47 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–47 can be utilized in microarrays or other assay formats, to screen collections of genetic material from patients who have a particular medical condition. These investigations can also be carried out using the sequences first disclosed in SEQ ID NOS:1–47 in silico and by comparing previously collected genetic databases and the disclosed sequences using computer software known to those in the art.

Thus the sequences first disclosed in SEQ ID NOS:1–47 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–47. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich. etc.), can optionally be used in conjunction with one or more discrete nucleotide sequence(s) present in the sequence that can be described by the relative position of the sequence relatve to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor, N.Y.).

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869, 336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequences of the described NHPs are presented in the Sequence Listing. SEQ ID NOS:1–19 describe sequences that are similar to mammalian sulfotransferases which can be found expressed in human cell lines, gene trapped cells and human testes cells. SEQ ID NO:19 describes a NHP ORF as well as flanking regions. The NHP nucleotides were obtained from human cDNA libraries using probes and/or primers generated from human gene trapped sequence tags. Expression analysis has provided evidence that the described NHP can be expressed in human testes and gene trapped human cells.

SEQ ID NOS:20–44 describe sequences that are similar to mammalian N-acetyl-galactosaminyltransferases. SEQ ID NO:44 describes a NHP ORF as well as flanking regions. The NHP nucleotides were obtained from human cDNA libraries using probes and/or primers generated from human gene trapped sequence tags. Expression analysis has provided evidence that the described NHPs are widely expressed.

SEQ ID NOS:45–47 describe sequences that are similar to mammalian transferase proteins. SEQ ID NO:47 describes a NHP ORF as well as flanking regions. The NHP nucleotides were obtained by aligning human gene trapped sequence tags with cDNA sequences obtained from human adipose, cerebellum, fetal brain, and rectum RNA samples, and marathon ready cDNA purchased from Clontech (Palo Alto, Calif.). Expression analysis has provided evidence that the described NHPs are widely expressed.

5.2 NHPS and NHP Polypeptides

NHPs, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, the identification of other cellular gene products related to a NHP, as reagents in assays for screening for compounds that can be as pharmaceutical reagents useful in the therapeutic treatment of mental, biological, or medical disorders and diseases. Given the similarity information and expression data, the described NHPs can be targeted (by drugs, oligos, antibodies, etc,) in order to treat disease, or to therapeutically augment the efficacy of, for example, chemotherapeutic agents used in the treatment of breast or prostate cancer.

The Sequence Listing discloses the amino acid sequences encoded by the described NHP polynucleotides. The NHPs typically display have initiator methionines in DNA sequence contexts consistent with a translation initiation site.

The NHP amino acid sequences of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., $E.$ $coli,$ $B.$ $subtilis$) transformed with recombinant bacteriophage DNA, plasmid DNA or cosmid DNA expression vectors containing NHP nucleotide sequences; yeast (e.g., $Saccharomyces,$ $Pichia$) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited to, the $E.$ $coli$ expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, $Autographa$ $californica$ nuclear polyhidrosis virus (AcNPV) is used as a vector to express foreign genes. The virus grows in $Spodoptera$ $frugiperda$ cells. A NHP coding sequence may be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect $Spodoptera$ $frugiperda$ cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$•nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in *Liposomes:A Practical Approach,* New,RRC ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ. This goal may be achieved by coupling of the NHP to a cytokine or other ligand that provides targeting specificity, and/or to a protein transducing domain (see generally U.S. applications Ser. Nos. 60/111,701 and 60/056,713, both of which are herein incorporated by reference, for examples of such transducing sequences) to facilitate passage across cellular membranes if needed and can optionally be engineered to include nuclear localization sequences when desired.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with a NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum.* Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl.

Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated polypeptide comprising the amino acid sequence of SEQ ID NO:43.

* * * * *